US011850364B2

(12) United States Patent
Dunn et al.

(10) Patent No.: US 11,850,364 B2
(45) Date of Patent: Dec. 26, 2023

(54) MANUFACTURED TO SHAPE HEADGEAR AND MASKS

(71) Applicant: ResMed Pty Ltd, Bella Vista (AU)

(72) Inventors: Jessica Lea Dunn, Scotts Head (AU); Justin John Formica, Sydney (AU); Anthony Paul Barbara, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 744 days.

(21) Appl. No.: 16/779,806

(22) Filed: Feb. 3, 2020

(65) Prior Publication Data

US 2020/0171262 A1 Jun. 4, 2020

Related U.S. Application Data

(63) Continuation of application No. 14/240,065, filed as application No. PCT/AU2012/000979 on Aug. 21, 2012, now Pat. No. 10,569,044.

(60) Provisional application No. 61/670,495, filed on Jul. 11, 2012, provisional application No. 61/526,057, filed on Aug. 22, 2011.

(51) Int. Cl.
*A61M 16/06* (2006.01)
*A62B 18/08* (2006.01)
*D04B 1/22* (2006.01)
*D04B 7/32* (2006.01)
*D04B 9/44* (2006.01)

(52) U.S. Cl.
CPC ........ *A61M 16/0683* (2013.01); *A61M 16/06* (2013.01); *D04B 1/225* (2013.01); *D04B 7/32* (2013.01); *D04B 9/44* (2013.01); *A61M 16/0633* (2014.02); *A61M 2016/0661* (2013.01); *A61M 2205/0216* (2013.01); *A61M 2207/00* (2013.01); *A62B 18/084* (2013.01)

(58) Field of Classification Search
CPC .. A61M 16/06; A61M 16/0683; A62B 18/084
USPC .................................................. 128/206.21
See application file for complete search history.

(56) References Cited

U.S. PATENT DOCUMENTS

| | | |
|---|---|---|
| 2,962,884 A | 12/1960 | Garrou |
| 3,299,908 A | 1/1967 | Petzetakis |
| 3,558,412 A | 1/1971 | Kurz |
| 3,570,482 A | 3/1971 | Emoto |
| 4,628,709 A | 12/1986 | Aeschbach et al. |
| 4,854,136 A | 8/1989 | Coslovi |
| 5,105,401 A | 4/1992 | Aoyagi et al. |

(Continued)

FOREIGN PATENT DOCUMENTS

| | | |
|---|---|---|
| AU | 2007278766 | 1/2008 |
| AU | 2008316306 | 4/2009 |

(Continued)

OTHER PUBLICATIONS

NV Further Examination Report dated Jun. 10, 2020 in corresponding NZ application 7563335.

(Continued)

*Primary Examiner* — Valerie L Woodward
*Assistant Examiner* — Paige Kathleen Bugg
(74) *Attorney, Agent, or Firm* — Nixon & Vanderhye P.C.

(57) ABSTRACT

A headgear or headgear segments are manufactured to shape thereby producing little or no waste material. Techniques such as knitting, braiding, crocheting, and 3D printing can be used produce the headgear.

20 Claims, 21 Drawing Sheets

(56) References Cited

U.S. PATENT DOCUMENTS

| | | | |
|---|---|---|---|
| 5,385,036 A * | 1/1995 | Spillane | D04B 21/18 |
| | | | 66/196 |
| 5,896,758 A | 4/1999 | Rock et al. | |
| 6,318,131 B1 | 11/2001 | Kobata et al. | |
| 6,332,465 B1 | 12/2001 | Xue | |
| 6,427,493 B1 | 8/2002 | Kasdan et al. | |
| 6,470,886 B1 | 10/2002 | Jestrabek-Hart | |
| 6,634,190 B2 | 10/2003 | Didier-Laurent | |
| 6,779,369 B2 | 8/2004 | Shepherd | |
| 6,907,882 B2 | 6/2005 | Ging et al. | |
| 6,931,762 B1 | 8/2005 | Dua | |
| 7,225,811 B2 | 6/2007 | Ruiz | |
| 7,240,522 B2 | 7/2007 | Kondou | |
| 7,497,097 B2 | 3/2009 | Herr | |
| 7,779,654 B2 * | 8/2010 | Garus | D04B 21/16 |
| | | | 66/196 |
| 7,779,832 B1 | 8/2010 | Ho | |
| 7,780,614 B2 | 8/2010 | Bruce et al. | |
| 8,109,271 B2 | 2/2012 | Vandline | |
| 8,286,634 B2 | 10/2012 | Madaus | |
| 8,297,285 B2 | 10/2012 | Henry et al. | |
| 8,424,530 B2 | 4/2013 | Gunaratnam et al. | |
| 8,505,538 B2 | 8/2013 | Amarasinghe | |
| 8,950,404 B2 | 2/2015 | Formica | |
| 9,308,339 B2 | 4/2016 | Sofranko | |
| 2002/0162597 A1 | 11/2002 | Radlinger et al. | |
| 2004/0040563 A1 | 3/2004 | Chu | |
| 2004/0067333 A1 | 4/2004 | Amarasinghe | |
| 2004/0083534 A1 | 5/2004 | Ruiz | |
| 2006/0090760 A1 * | 5/2006 | Gradon | A61M 16/0633 |
| | | | 128/207.11 |
| 2006/0277951 A1 * | 12/2006 | Herr | D04B 21/12 |
| | | | 66/196 |
| 2007/0144221 A1 * | 6/2007 | Sytz | D04B 1/18 |
| | | | 66/171 |
| 2007/0181135 A1 | 8/2007 | Baker | |
| 2007/0246043 A1 | 10/2007 | Kwok et al. | |
| 2008/0006060 A1 | 1/2008 | Park et al. | |
| 2008/0047560 A1 | 2/2008 | Veliss | |
| 2008/0060649 A1 | 3/2008 | Veliss et al. | |
| 2008/0060654 A1 | 3/2008 | Vandine | |
| 2008/0110049 A1 | 5/2008 | Sokolowski et al. | |
| 2008/0115788 A1 | 5/2008 | Eschen et al. | |
| 2008/0142015 A1 | 6/2008 | Groll | |
| 2009/0173343 A1 | 7/2009 | Omura | |
| 2009/0192430 A1 * | 7/2009 | Evans | A61F 13/04 |
| | | | 602/76 |
| 2009/0217929 A1 | 9/2009 | Kwok et al. | |
| 2009/0223518 A1 * | 9/2009 | Kwok | A61M 16/0683 |
| | | | 128/205.25 |
| 2009/0267261 A1 | 10/2009 | Mark | |
| 2010/0000544 A1 | 1/2010 | Blaszczykiewicz | |
| 2010/0018534 A1 | 1/2010 | Veliss et al. | |
| 2010/0154256 A1 | 6/2010 | Dua | |
| 2010/0224195 A1 | 9/2010 | Henry | |
| 2010/0229868 A1 | 9/2010 | Rummery | |
| 2010/0258132 A1 | 10/2010 | Moore | |
| 2010/0258136 A1 | 10/2010 | Doherty | |
| 2010/0269372 A1 | 10/2010 | Dua et al. | |
| 2010/0307502 A1 | 12/2010 | Rummery et al. | |
| 2010/0312160 A1 | 12/2010 | Creighton et al. | |
| 2011/0072553 A1 | 3/2011 | Ho | |
| 2011/0078921 A1 | 4/2011 | Greene et al. | |
| 2011/0146685 A1 | 6/2011 | Allan et al. | |
| 2011/0197341 A1 | 8/2011 | Formica et al. | |
| 2011/0253143 A1 | 10/2011 | Ho | |
| 2012/0082807 A1 | 4/2012 | Malloy | |
| 2012/0132209 A1 | 5/2012 | Park et al. | |
| 2014/0209098 A1 | 7/2014 | Dunn et al. | |

FOREIGN PATENT DOCUMENTS

| | | | | |
|---|---|---|---|---|
| AU | 2009326861 | | 6/2010 | |
| CN | 1213277 A | | 4/1999 | |
| CN | 1352532 A | | 6/2002 | |
| CN | 101495170 | | 7/2009 | |
| CN | 101516427 | | 8/2009 | |
| CN | 101687085 | | 3/2010 | |
| CN | 101951984 | | 1/2011 | |
| CN | 102245250 | | 11/2011 | |
| CN | 102698349 | | 10/2012 | |
| EP | 0 875 612 A2 | | 11/1998 | |
| EP | 2046430 | | 4/2009 | |
| EP | 2051760 | | 4/2009 | |
| EP | 2083897 | | 8/2009 | |
| EP | 2101855 | | 9/2009 | |
| EP | 2 140 902 A1 | | 1/2010 | |
| EP | 2428240 | | 3/2012 | |
| EP | 2428241 | | 3/2012 | |
| EP | 2425868 | | 7/2012 | |
| EP | 2481434 | | 8/2012 | |
| EP | 2481435 | | 8/2012 | |
| EP | 2022528 B1 * | | 3/2016 | A61M 16/06 |
| GB | 2 200 281 A | | 8/1988 | |
| JP | 10-310907 A | | 11/1998 | |
| JP | A-2003-325687 | | 11/2003 | |
| JP | 2004-000572 | | 1/2004 | |
| JP | 3660036 B2 | | 3/2005 | |
| JP | 2008-519652 A | | 6/2008 | |
| JP | 2009544371 | | 12/2009 | |
| JP | 2009544372 | | 12/2009 | |
| JP | 2010-509942 A | | 4/2010 | |
| JP | 2010512193 | | 4/2010 | |
| JP | 2011500229 | | 1/2011 | |
| JP | T-2011-521732 | | 7/2011 | |
| JP | 2012-511341 | | 5/2012 | |
| JP | 2012511341 | | 5/2012 | |
| JP | 2012-513231 A | | 6/2012 | |
| NZ | 567432 | | 3/2012 | |
| NZ | 575405 | | 9/2012 | |
| WO | WO-9962440 A1 * | | 12/1999 | A61F 13/04 |
| WO | WO 2000/074509 | | 12/2000 | |
| WO | WO 2003/082550 | | 10/2003 | |
| WO | WO-2006015599 A1 * | | 2/2006 | |
| WO | WO 2007/114492 A1 | | 10/2007 | |
| WO | WO 2008/011682 | | 1/2008 | |
| WO | WO 2008/011683 | | 1/2008 | |
| WO | WO 2008/070929 | | 6/2008 | |
| WO | WO 2009/026627 A1 | | 3/2009 | |
| WO | WO 2009/052560 | | 4/2009 | |
| WO | WO-2009052560 A1 * | | 4/2009 | |
| WO | WO 2009/059353 | | 5/2009 | |
| WO | WO 2010/066004 | | 6/2010 | |
| WO | WO-2010066004 A1 * | | 6/2010 | |
| WO | WO 2010/073138 A1 | | 7/2010 | |
| WO | WO 2010/073142 | | 7/2010 | |
| WO | WO 2010/131189 | | 11/2010 | |
| WO | WO 2011/014931 | | 2/2011 | |
| WO | WO 2011/048510 | | 4/2011 | |
| WO | WO 2011/059346 | | 5/2011 | |
| WO | WO-2012008305 A2 * | | 4/2012 | |
| WO | WO 2012/085755 | | 6/2012 | |
| WO | WO-2012080887 A2 * | | 6/2012 | |
| WO | WO 2012/167327 A1 | | 12/2012 | |

OTHER PUBLICATIONS

Chinese Office Action and English translation dated Jun. 28, 2020 in corresponding Chinese Patent Application 201710059112.8.
EP Summons to attend oral proceedings pursuant to Rule 115(1) EPC in corresponding EP Application 12825595.7.
European Search Report dated Apr. 9, 2021 in corresponding EP Application 21156279.8 (9 pages).
NZ First Examination Report dated Feb. 19, 2021 in corresponding NZ Application 772753 (5 pages).
Final Office Action dated Oct. 13, 2021 in corresponding U.S. Appl. No. 17/111,801 (16 pages).
Simple Sock Making; simplesockmaking.com (Year: 2009).
On The Edge; tessknits.com (Year: 2009).
Tuck Stitch; Stitches produced by varying the sequence of the needle loop intermeshing; David J. Spencer; Knitting Technology (Third Edition) (Year: 2001).

(56) References Cited

OTHER PUBLICATIONS

Home made Helmet-Liner, Nov. 2009.
Helmetliner, Aunt B @2005.
Additive-manufacturing.
Fuges, 30-printing-for; Apr. 2012.
Second Chinese Office Action and English translation thereof dated Aug. 27, 2019 in corresponding CN Application 201710059112.8.
NZ First Examination Report dated Sep. 11, 2019 in corresponding NZ Application 756335.
JP Report on the Reexamination Prior To Trial and English translation thereof dated Sep. 13, 2019 in corresponding JP Application 2017-110750.
Japanese Decision of Rejection and English translation thereof dated Feb. 25, 2019 in corresponding JP Patent Application 2017-110750.
First Office Action issued in corresponding Chinese Application No. 201710059112.8 dated Nov. 12, 2018, with English translation, (11 pages).
Examination Report in New Zealand Application No. 749815 dated Jan. 17, 2019 (5 pages).
A Second Office Action issued in corresponding Japanese Application No. 2014-526338, with English translation, dated Jul. 23, 2018, (5 pages).
A Communication pursuant to Article 94(3) EPC dated Jul. 10, 2018, in corresponding European Patent Application No. 12 825 595.7 (5 pages).
A Decision of Rejection dated Jun. 19, 2018, in a corresponding Japanese Patent Application No. 2017-110750 (4 pages), and an English translation thereof (7 pages).
A Communication pursuant to Article 94(3) EPC dated Jan. 22, 2018, in corresponding European Patent Application No. 12 825 595.7 (5 pages).
A Pre-Appeal Examination Report dated Aug. 22, 2017, in a corresponding Japanese Application No. 2014-526338 (2 pages), with an English translation thereof (3 pages).
A Deadline for Counterstatement dated Sep. 11, 2017, with a Statement of Case, First Amended Notice of Opposition (clean and marked up versions), in a corresponding New Zealand Application No. 621617 (35 pages).
A First Examination Report dated Aug. 1, 2017, in a corresponding New Zealand Patent Application No. 733539 (5 pages).
A Further Examination Report dated May 23, 2017 in a corresponding New Zealand Application No. 715772 (2 pages).
Proceeding Correspondence dated May 10, 2017, in a corresponding New Zealand Application No. 621617 (4 pages).
A Decision of Rejection dated Jan. 27, 2017, in a corresponding Japanese Application No. 2014-526338 (4 pages), and an English translation thereof (6 pages), citing Japanese Publication No. JP2002-253725.
Patent Examination Report No. 1 dated Aug. 24, 2016, in a corresponding Australian Patent Application No. 2015218417 (3 pages).
Notice of Opposition to Grant of Patent (Section 21) and Application under Regulation 168 for Extension of Time filed Jun. 24, 2016 in a corresponding New Zealand Application No. 621617 (4 pages).
A First Office Action dated May 23, 2016, in a corresponding Japanese Application No. 2014-526338 (7 pages), and an English translation thereof (7 pages).
Notification of Second Office Action dated Feb. 6, 2016 in a corresponding Chinese patent application No. 201280051409.5 (8 pages), and an English translation thereof (8 pages).
First Examination Report dated Jan. 21, 2016, in a corresponding New Zealand Patent Application No. 715772 (3 pages).
Further Examination Report dated Jan. 21, 2016 in a corresponding New Zealand Application No. 621617 (2 pages).
Patent Examination Report No. 3 dated Aug. 21, 2015, in a corresponding Australian Application No. 2012300183 (6 pages).
A First Office Action dated Jul. 2, 2015 in a corresponding Chinese Application No. 201280051409.5 (10 pages) and the English translation thereof (9 pages).
Extended European Search Report dated Mar. 30, 2015 issued in corresponding European Patent Application No. 12825595.7 (8 pages).
Patent Examination Report No. 1 dated Aug. 26, 2014 in corresponding Australian Patent Application No. 2012300183.
First Examination Report dated Jul. 29, 2014 in corresponding New Zealand Application No. 621617.
Unsolicited Email from Elson Silva, PhD, "Protecting Hydrology Science from Reinvention by Fake Scientists and Corrupt Lawyers/ Wicking Mob," dated Jul. 31, 2014.
International Search Report for PCT/AU2012/000979, dated Dec. 5, 2012.
Janne Kyttanen; Freedom of Creation Store; http://www.freedomofcreation.com/shop/order.php?cat=30; 2011.
Continuum Fashion; http://www.continuumfashion.com/N12.html, before Applicant's filing date.
Gohl et al.; "Textiles for Modern Living," Third Edition; pp. 162, 163 and 210-219 and 228-233, before Applicant's filing date.
Nose Warmer, Nose Cover, Cold Nose No More, Nose Cozy, Crocheted; http://www.etsy.com/transaction 12456988, before Applicant's filing date.
De Araujo et al.; Modelling and Simulation of the Mechanical Behaviour of Weft-Knitted Fabrics for Technical Applications, before Applicant's filing date.
Gries et al.; "New Developments on Manufacturing Fibers and Textile Structures for Technical Textiles," before Applicant's filing date.
Technical Textiles—Stoll Brochure, before Applicant's filing date.
Riley; "Rapid Prototyping Fabric Sculptures," Thesis; Spring, 2007.
www.dyneema.com printout, before Applicant's filing date.
Bandagen und Orthesen; Product catalogue; www.bauerfeind.com, Feb. 2011.
Echelman, "Taking Imagination Seriously," before Applicant's filing date.
Techtextil: Steiger targets technical textile markets; http://www.innovationintextiles.com/articles/894.php, May 31, 2011.
Choi et al., "Three Dimensional Seamless Garment Knitting on V-Bed Flat Knitting Machines," Journal of Textile and Apparel, Technology and Management, vol. 4, Issue 4, Spring 2005.
PURE® by Lankorst printout, before Applicant's filing date.
Abounaim, Dissertation, "Process Development for the Manufacturing of Flat Knitted Innovative 3D Spacer Fabrics for High Performance Composite Applications," before Applicant's filing date.
Innovation in Textiles News: Shaped Spacer Fabrics for Tailor Made Solutions; http://www.innovationintextiles.com/articles/246.php, Oct. 1, 2009.
Bruer et al., "Three-Dimensionally Knit Spacer Fabrics: A Review of Production Techniques and Application," Journal of Textile and Apparel, Technology and Management, vol. 4, Issue 4, Summer 2005.
Written Opinion of the International Searching Authority issued in PCT Application No. PCT/AU2012/000979 dated Dec. 5, 2012.
International Search Report issued in PCT Application No. PCT/AU2012/000979 dated Dec. 5, 2012.
Niri, Hydrospace; http://www.nonwovens-innovation.com/hydrospace.html, 2011.
NZ Further Examination Report dated Dec. 12, 2019 in corresponding NZ Application 756335.
Fujimura, "Development of non-sewn well-knitwear WHOLEGARMENT", [online], Jul. 25, 2003, Textile Machinery Society, [Search on Aug. 28, 2020] the Internet URL:https://www.jstage.ist.co.jp/article/transitmsj1972/56/7/56_7_P305/_pdf/-char/ja (6 pages).
JP Notice of Reasons for Rejection dated Sep. 7, 2020 in corresponding JP Application 2019-117622 and English translation thereof (8 pages).
EP Search Report dated May 7, 2021 in corresponding EP Application 21156294.7 (7 pages).
Office Action dated Jun. 7, 2021 in corresponding U.S. Appl. No. 17/111,801 (16 pages).
Office Action dated Apr. 26, 2021 in corresponding JP Patent Application 2019-117622 (5 pages).

(56) References Cited

OTHER PUBLICATIONS

Chinese Office Action and English translation dated Feb. 6, 2020 in corresponding Chinese Patent Application 201710059112.8.
JP Notice of Reasons for Rejection dated Sep. 12, 2022 in corresponding JP Application 2021-155710 (8 pages).
NZ First Examination Report dated Aug. 11, 2022 in corresponding NZ Application 790440 (5 pages).

* cited by examiner

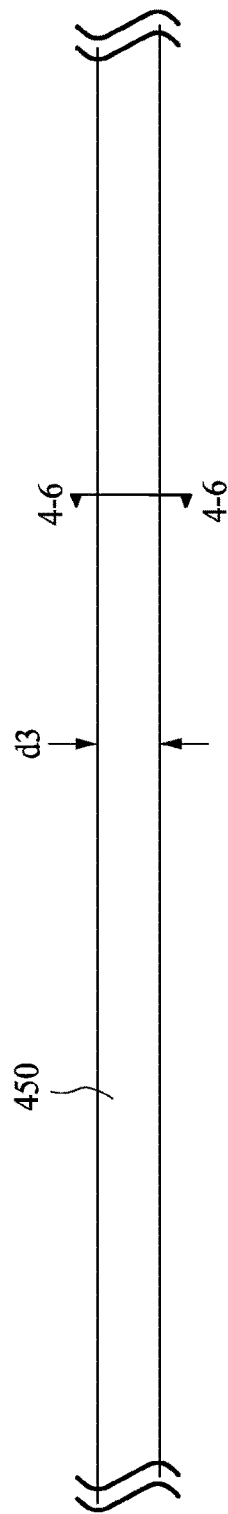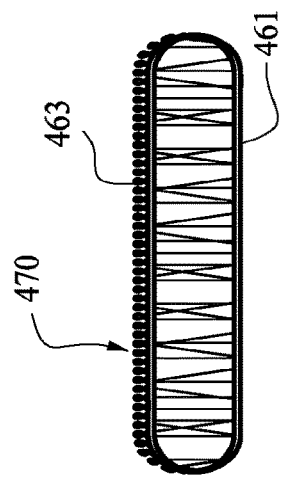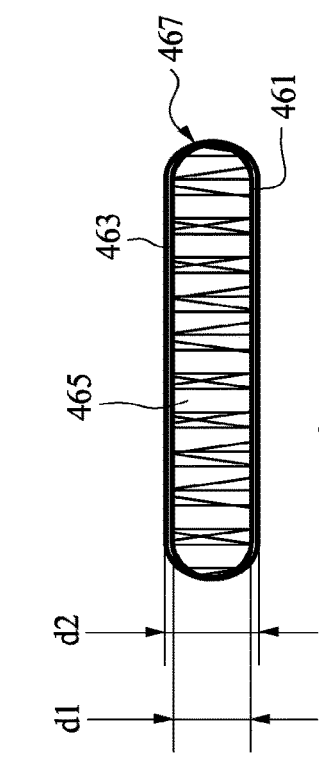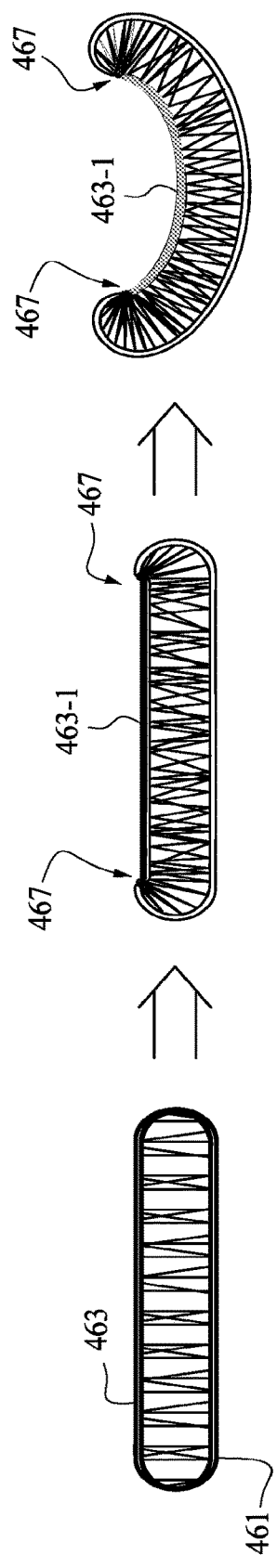

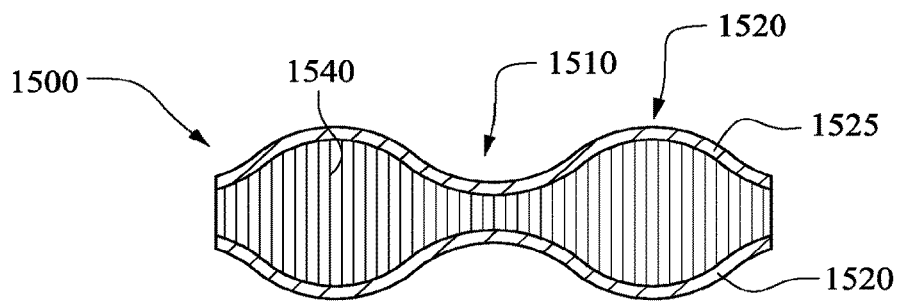
Fig. 15-1
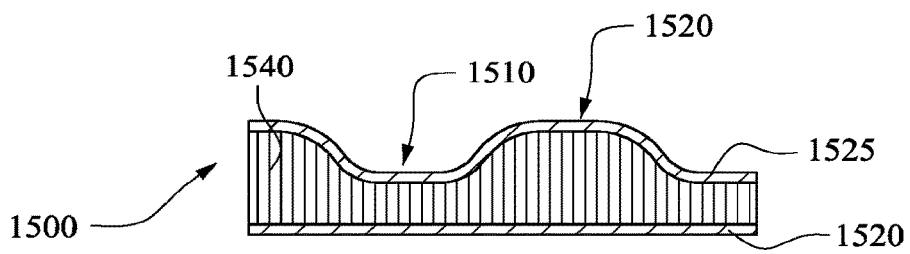
Fig. 15-2
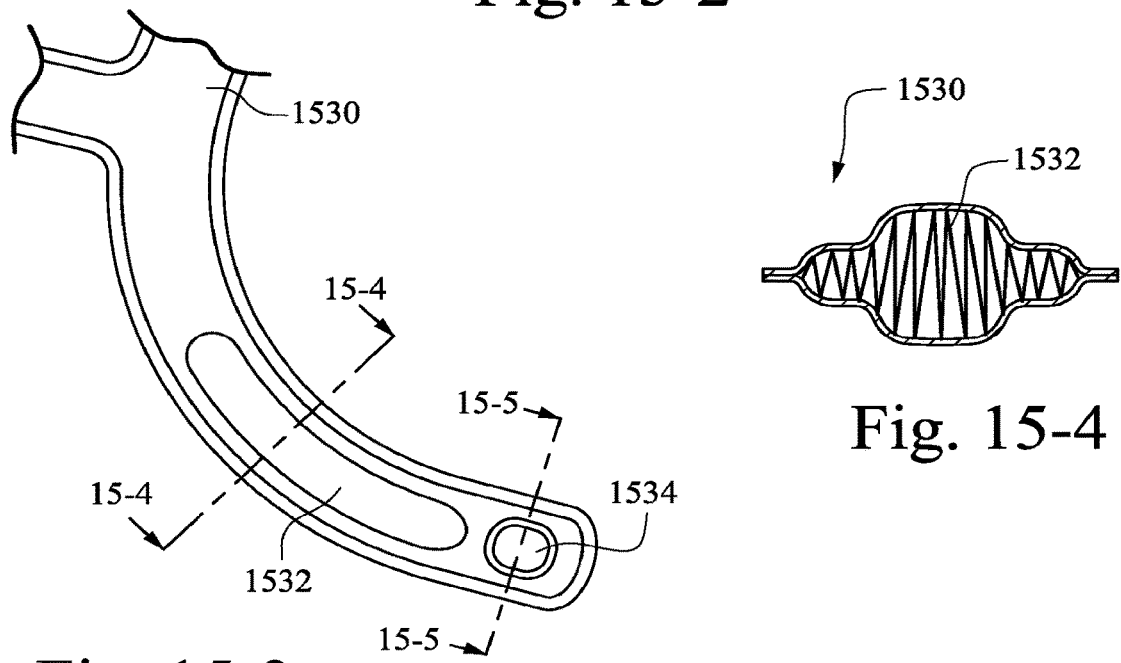
Fig. 15-3
Fig. 15-4
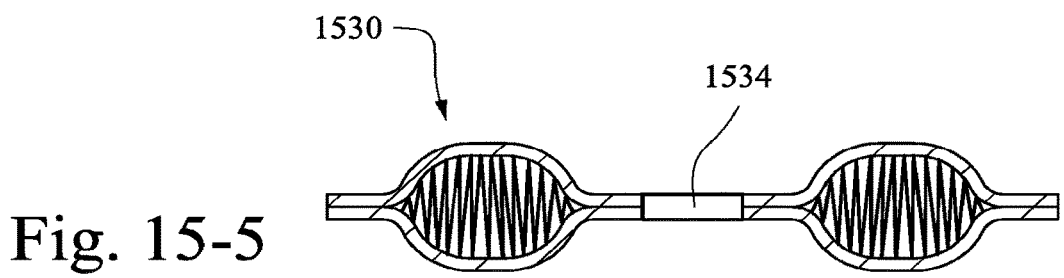
Fig. 15-5

MANUFACTURED TO SHAPE HEADGEAR AND MASKS

CROSS-REFERENCE TO APPLICATION

This application is a continuation of U.S. patent application Ser. No. 14/240,065 filed Feb. 21, 2014 (allowed), which is the U.S. national phase of International Application PCT/AU2012/000979, filed Aug. 21, 2012 which designated the U.S. and claims the benefit of U.S. Provisional Application No. 61/670,495, filed Jul. 11, 2012 and U.S. Provisional Application No. 61/526,057, filed Aug. 22, 2011. Each application mentioned above is incorporated herein by reference in its entirety.

FIELD OF TECHNOLOGY

The present technology relates to headgear and masks, and a method of manufacturing such for use in treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

Masks used for treatment of SDB such as Obstructive Sleep Apnea (OSA) are typically held on a patient's head by headgear. Headgear typically includes one or more headgear straps that are adapted to engage with the mask and hold the mask in position on the patient's face. In addition, headgear should be comfortable so that a patient can wear the mask at night while they sleep. There is a continuous need in the art for headgear that is comfortable, fits a wide range of patients, is easily manufactured, and is inexpensive.

Known methods of manufacturing headgear involve cutting headgear components 1020 from a sheet of fabric 1000, as shown in FIG. 1. A problem with this method is that it renders a relatively large portion of the sheet 1000 to waste. While waste can be minimized by nesting the headgear pieces as closely as possible on the sheet 1000, the cutting step required in this process ensures that waste material will be produced. In manufacturing headgear in a conventional manner, several different materials and several different manufacturing processes must be used. In manufacturing headgear, considerable time and labor is required to cut the components and sub-components to an appropriate size and shape, and to stitch or bond or laminate these elements to each other. These techniques are time, labor, and process intensive, and the cutting or trimming process usually results in an undesirable amount of waste compared to the part of the material actually used, even with appropriate nesting of components.

SUMMARY OF TECHNOLOGY

An aspect of the disclosed technology relates to a fabric component for use with a mask system.

Another aspect of the disclosed technology relates to a headgear for use with a mask system.

Another aspect of the disclosed technology relates to headgear for use in supporting a respiratory mask in position on a patient's face for positive pressure treatment of the patient, wherein the headgear comprises at least one component (e.g., strap, crown portion, other head/face contacting portions) formed of a single unitary, seamless structure.

Another aspect of the disclosed technology relates to knitting various headgear sections in a continuous manner so that there are no or very few additional manufacturing steps that would be required to sew, fuse, adhere or otherwise attach adjoining sections. As a result, the manufacturing process may have reduced steps, the amount of material waste is reduced, there would be virtually no seams in the headgear between the adjoining sections, and the headgear made of a fabric without distinctive joins or seams may be more comfortable for patients.

Another aspect of the disclosed technology relates to knitting various headgear sections in a continuous manner i.e. forming a single, unitary seamless structure having at least two regions, wherein the at least two regions extend from a junction at different angular orientations. For example, a first strap may extend in a substantially horizontal direction and a second strap may extend in a substantially vertical direction, the first strap and the second strap being formed as a single, unitary seamless structure formed in a continuous process (e.g. knitting).

Another aspect of the disclosed technology relates to knitting various headgear sections in a continuous manner i.e. forming a single, unitary seamless structure having at least two regions, wherein the at least two regions branch out or extend at different angles or in different directions to one another.

Another aspect of the disclosed technology relates to a headgear for a mask, the headgear being constructed of a textile formed from mechanically manipulated yarn.

A further aspect of the disclosed technology relates to a headgear for a mask, the headgear being constructed of a textile formed from mechanically manipulated yarn by interlooping, including knitting.

A further aspect of the disclosed technology relates to a headgear for a mask, the headgear being constructed of a textile formed from mechanically manipulated yarn by interweaving.

A further aspect of the disclosed technology relates to a headgear for a mask, the headgear being constructed of a textile formed from mechanically manipulated yarn by intertwining, including braiding and knotting.

Another aspect of the disclosed technology relates to a method of manufacturing headgear comprising forming a textile to shape (e.g., formed in one piece to shape without cutting, by mechanical manipulation of yarn including means of but not limited to interlooping, interweaving, intertwining, including for example knitting, crochet, braiding, weaving or additive manufacturing/3D printing), wherein the textile is adapted to support, in use, a mask on a patient's face.

Another aspect of the disclosed technology relates to headgear for use in supporting a respiratory mask in position on a patient's face for positive pressure treatment of the patient, wherein the headgear comprises a strap at least partly constructed of spacer fabric.

Another aspect of the disclosed technology relates to headgear for use in supporting a respiratory mask in position on a patient's face for positive pressure treatment of the patient, wherein the headgear comprises a strap at least partly constructed of spacer fabric, the spacer fabric being formed by a first and second ground layer or structure, the first and second ground layers or structures being substantially parallel.

Another aspect of the disclosed technology relates to headgear for use in supporting a respiratory mask in position on a patient's face for positive pressure treatment of the patient, wherein the headgear comprises a strap at least partly constructed of spacer fabric, the spacer fabric being formed by a first and second ground layer or structure, the first and second ground layers or structures being substantially parallel, the first and second ground layers or structures having different stiffnesses.

Another aspect of the disclosed technology relates to headgear for use in supporting a respiratory mask in position on a patient's face for positive pressure treatment of the patient, wherein the headgear comprises a strap at least partly constructed of spacer fabric, the spacer fabric being formed by a first and second ground layer or structure, and further comprising a traversing or floating yarn or pile adapted to connect the first and second ground layers or structures.

Another aspect of the disclosed technology relates to headgear for use in supporting a respiratory mask in position on a patient's face for positive pressure treatment of the patient, wherein the headgear comprises a strap at least partly constructed of spacer fabric, wherein the spacer fabric is formed by knitting.

Another aspect of the disclosed technology relates to headgear for use in supporting a respiratory mask in position on a patient's face for positive pressure treatment of the patient, wherein the headgear comprises a strap at least partly constructed of spacer fabric, wherein an outer surface of the headgear may be formed from, for example, about 30-100, 20-300, or 50-200 denier yarn for a pleasant hand feel.

Another aspect of the disclosed technology relates to headgear for use in supporting a respiratory mask in position on a patient's face for positive pressure treatment of the patient, wherein the headgear comprises at least a first yarn and a second yarn, the first yarn having a first stiffness and the second yarn having a second stiffness.

Another aspect of the disclosed technology relates to headgear for use in supporting a respiratory mask in position on a patient's face for positive pressure treatment of the patient, wherein the headgear is formed by flat knitting or circular knitting.

Another aspect of the disclosed technology relates to headgear for use in supporting a respiratory mask in position on a patient's face for positive pressure treatment of the patient, wherein the headgear is formed by flat knitting. The headgear may further comprise pockets, tunnels, layers and/or ribs. Furthermore, the pockets or tunnels may be reinforced with stiffer materials to add rigidity to the headgear.

Another aspect of the disclosed technology relates to headgear for use in supporting a respiratory mask in position on a patient's face for positive pressure treatment of the patient, wherein the headgear is formed by flat knitting or circular knitting. The headgear may further comprise pockets, tunnels, layers and/or ribs. The pockets or tunnels may be cushioned by filling the pockets or tunnels with padding, including floating yarn, looped yarn, foam or other cushioning material.

Another aspect of the disclosed technology relates to headgear for use in supporting a respiratory mask in position on a patient's face for positive pressure treatment of the patient, wherein the headgear is formed by flat knitting or circular knitting, further wherein the headgear has selvedges, that is, ends of the yarn are distal to the edge of the headgear to prevent unraveling or fraying.

Another aspect of the disclosed technology relates to headgear for use in supporting a respiratory mask in position on a patient's face for positive pressure treatment of the patient, wherein the headgear is formed by a regular or irregular pique knit so the yarn exposed on the right side is different to the yarn exposed on the wrong side. For example, the yarn on the right side may have a pleasant visual appearance and the yarn on the wrong side may have a nice hand feel for contacting the patient's skin. Alternatively, or in addition, the yarn on the right side may have a first moisture wicking property and the wrong side may have a second moisture wicking property. For example, the yarn on the right side may have a high percentage of microfiber having a first moisture wicking property and the wrong side may have a high percentage of non-microfiber having a second moisture wicking property.

Another aspect of the disclosed technology relates to a headgear for use in supporting a respiratory mask in position on a patient's face, the headgear being constructed of a yarn, the headgear having a first region with a first density of yarn and a second region with a second density of yarn. The region with the greater density of yarn may have less extensibility, less permeability and higher stiffness.

Another aspect of the disclosed technology relates to a headgear for use in supporting a respiratory mask in position on a patient's face, the headgear being constructed of a first yarn and a second yarn, the headgear having a first region constructed of the first yarn, the first yarn having a first denier and a second region constructed of the second yarn, the second yarn having a second denier.

Another aspect of the disclosed technology relates to a headgear for use in supporting a respiratory mask in position on a patient's face, the headgear being constructed of a first yarn and a second yarn, the headgear having a first region constructed of the first yarn, the first yarn having a first twist per inch property and a second region constructed of the second yarn, the second yarn having a second twist per inch property.

Another aspect of the disclosed technology relates to a headgear for use in supporting a respiratory mask in position on a patient's face, the headgear being constructed of a yarn, the yarn comprising textured filaments. The textured filaments may improve hand feel and alter the stretch characteristics of the headgear.

Another aspect of the disclosed technology relates to a method of forming a headgear for use in supporting a respiratory mask in position on a patient's face, comprising the steps of knitting the headgear with a water soluble yarn, dissolving at least an edge of the headgear in water, and drying the headgear (thereby causing it to shrink). The shrinkage of the edge of the headgear may result in a finished edge.

Another aspect of the disclosed technology relates to a method of forming headgear for use in holding a respiratory mask in position on a patient's face and comprising a) knitting a yarn or thread to form a headgear component (e.g., a strap) adapted to at least partially support the mask, the component being connected to an attachment member, the attachment member adapted to connect the component to the mask; and in step a), looping the yarn or thread through a connecting portion formed in the attachment member to connect the component to the attachment member.

Another aspect of the disclosed technology relates to a mask system for use in treating a patient for sleep disordered breathing comprising a mask assembly adapted to seal against the patient's face thereby forming a breathing cavity, the mask having one or more portions constructed of a first knitted fabric; and a headgear connected to the mask to at least partially support the mask on the patient's face, the headgear having one or more portions constructed of at least one of the first knitted fabric and a second knitted fabric.

Another aspect of the disclosed technology relates to a mask system for use in treating a patient for sleep disordered breathing comprising a mask assembly adapted to seal against the patient's face thereby forming a breathing cavity, the mask having one or more portions constructed of a first knitted fabric; and a headgear connected to the mask to at least partially support the mask on the patient's face, the headgear having one or more portions constructed of at least one of the first knitted fabric and a second knitted fabric. The first knitted fabric may be joined to the second knitted fabric by interlooping and preferably having a seamless connection or join, for example a tuck stitch.

Another aspect of the disclosed technology relates to a method of forming headgear for use in holding a respiratory mask in position on a patient's face and comprising knitting a yarn or thread to form a headgear component adapted to at least partially support the mask, wherein a grain or course of the knit is altered to form a curved portion of the headgear component.

Another aspect of the disclosed technology relates to a method of forming headgear for use in holding a respiratory mask in position on a patient's face and comprising knitting a yarn or thread to form a headgear component adapted to at least partially support the mask, wherein a grain or course of the knit is arranged to allow or disallow stretch in at least one portion of the headgear component.

Another aspect of the disclosed technology relates to headgear for use in supporting a respiratory mask in position on a patient's face for positive pressure treatment of the patient, the headgear comprising a first component at least partly constructed of spacer fabric, the spacer fabric including an inner fabric, an outer fabric and an inner spacer fiber interconnecting the outer fabric and the inner fabric, wherein the inner fabric delimits a hollow interior area.

Another aspect of the disclosed technology relates to a method of forming headgear for use in holding a respiratory mask in position on a patient's face, comprising knitting a yarn or thread to form a headgear component adapted to at least partially support the mask, the headgear component being at least partly constructed of spacer fabric and having an inner layer formed of spacer yarns; and altering a length or density of the spacer yarns in at least one portion of the headgear component to vary an attribute of the headgear component.

Another aspect of the disclosed technology relates to a mask assembly for use in treating a patient for sleep disordered breathing comprising one or more portions constructed of spacer fabric, the spacer fabric having an inner layer formed of spacer yarns, the inner layer having at least one portion forming a vent hole, wherein the at least one portion is substantially void of spacer yarns.

Another aspect of the disclosed technology relates to a method of forming headgear for use in holding a respiratory mask in position on a patient's face and comprising knitting a yarn or thread to form a first knitted fabric; concurrently knitting a yarn or thread to form a second knitted fabric; and at the same time, knitting the first knitted fabric to the second knitted fabric such that one of the first knitted fabric and the second knitted fabric forms an inner fabric adapted to interface with the patient.

Another aspect of the disclosed technology relates to a method of forming headgear for use in holding a respiratory mask in position on a patient's face and comprising knitting a yarn or thread to form a headgear component adapted to at least partially support the mask; and altering a number of stitches in at least one portion of the headgear component to vary an attribute of the headgear component.

Another aspect of the disclosed technology relates to a method of forming headgear for use in holding a respiratory mask in position on a patient's face and comprising knitting a yarn or thread to form a headgear component adapted to at least partially support the mask; and altering a thread count or stitch style in at least one portion of the headgear component to vary an attribute of the headgear component.

Another aspect of the disclosed technology relates to a headgear assembly for use in supporting a respiratory mask in position on a patient's face for positive pressure treatment of the patient, the headgear comprising a first headgear component constructed of a knitted fabric, the knitted fabric including a first yarn or thread and a second yarn or thread having a higher stiffness than the first yarn or thread, wherein the second yarn or thread is arranged to provide a rigidizing portion of the first headgear component.

Another aspect of the disclosed technology relates to a method of forming headgear for use in holding a respiratory mask in position on a patient's face and comprising providing a base headgear material to form a headgear component adapted to at least partially support the mask; and then either (but not limited to) knitting, embroidering or weaving a yarn or thread into the base headgear material, the yarn or thread having a higher stiffness than the base material, wherein the yarn or thread is arranged to provide a rigidizing portion of the headgear component.

Another aspect of the disclosed technology relates to a headgear assembly for use in supporting a respiratory mask in position on a patient's face for positive pressure treatment of the patient, the headgear comprising a first yarn, the first yarn being formed from a thermoplastic, wherein the thermoplastic yarn may be fused to create a rigidized portion of the headgear component.

Another aspect of the disclosed technology relates to a method of forming headgear for use in holding a respiratory mask in position on a patient's face and by using "additive manufacturing" or "rapid manufacture" or "3D printing" processes (these terms are able to be used interchangeably in colloquial language) to create a textile which forms at least a first headgear component adapted to at least partially support the mask.

Still another aspect of the disclosed technology relates to a method of manufacturing custom headgear for use in holding a respiratory mask in position on a patient's face and comprising acquiring data related to the shape and size of the patient's head; creating an electronic headgear model with a computing device and computer aided design program in accordance with the acquired data; and forming at least a first headgear component corresponding at least in part to the electronic headgear model.

Another aspect of the disclosed technology relates to a method of manufacturing a series of headgear for use in holding a respiratory mask in position on a patient's face and comprising knitting a first headgear or headgear component, knitting a knit release, knitting a second headgear or headgear component and separating the first headgear or headgear component from the second headgear or headgear component at the knit release.

Another aspect of the disclosed technology relates to a component (e.g., headgear, mask, tube, cushion) that may be formed via processes such as knitting, weaving, crochet or embroidery in order to include the use of one or several types of yarns with various unique properties, such as conductivity. For example, a conductive yarn or thread which is integrated into the overall form of the component might be used for conveying electricity and/or data to and from, for example, similarly integrated or add-on: sensors, heating elements, cooling elements, tensioning systems, on/off buttons, power sources, computer chips, controllers etc.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of this technology. In such drawings:

FIG. 4-1 shows a process of forming headgear straps from a continuous roll according to an example of the disclosed technology;

FIG. 4-2 shows a strap according to an example of the disclosed technology;

FIG. 4-3 is a cross-sectional view along the line 4-3 to 4-3 of FIG. 4-2;

FIG. 4-4 is a cross-sectional view of a strap according to an alternative example of the disclosed technology;

FIG. 4-5 shows a strap according to an example of the disclosed technology;

FIG. 4-6 is a cross-sectional view along the line 4-6 to 4-6 of FIG. 4-5;

FIG. 4-7 is a cross-sectional view of a strap according to an alternative example of the disclosed technology;

FIG. 4-8 is a cross-sectional view of a strap according to an alternative example of the disclosed technology;

FIG. 5-1 is a perspective view showing attachment of headgear to a mask in according to an example of the disclosed technology;

FIG. 5-2 shows a lower headgear clip according to an example of the disclosed technology;

FIG. 6 is a front view of an integral headgear and mask system in position on a patient's head according to an example of the disclosed technology;

FIGS. 7 and 8 are conventional examples depicting the knitting process;

FIG. 9-1B is a schematic representation of the basic warp knitted fabric of FIG. 9-1A;

FIG. 9-2 illustrates a basic warp knitted fabric according to an example of the disclosed technology;

FIGS. 14-1 to 14-4 shows one way of manufacturing headgear formed as a tube via circular warp knitting according to examples of the disclosed technology;

FIG. 14-5 is a cross-sectional view of a strap according to an example of the disclosed technology;

FIG. 14-6 is partial view of a strap according to an example of the disclosed technology;

FIG. 14-6A is a cross-sectional view along the line 14-6A-14-6A in FIG. 14-6;

FIGS. 15-1 to 15-5 show headgear including portions having variable thicknesses according to examples of the disclosed technology;

FIG. 22-1 is a schematic representation of a double knit headgear or mask component according to an example of the disclosed technology;

FIGS. 22-2A and 22-2B illustrate an interlock knit headgear or mask component according to an example of the disclosed technology;

FIG. 25-1 is a side view of headgear including a rigidizer in position on a patient's head according to an example of the disclosed technology;

FIG. 25-2 is an enlarged view of the headgear of FIG. 25-1;

DETAILED DESCRIPTION OF ILLUSTRATED EXAMPLES

The following description is provided in relation to several examples which may share common characteristics and features. It is to be understood that one or more features of any one example may be combinable with one or more features of the other examples. In addition, any single feature or combination of features in any of the examples may constitute an additional example or examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

1. Headgear

The figures illustrate headgear according to examples of the disclosed technology. In the illustrated examples, headgear are adapted to be removably attached to a patient interface to hold and maintain the patient interface in a desired position on a patient's face. While headgear may be illustrated as being used with a particular type of patient interface (e.g., mask), it should be appreciated that each headgear may be adapted for use with other suitable patient interfaces. That is, the patient interfaces are merely exemplary, and each headgear embodiment may be adapted for use with any suitable patient interface, e.g., full-face mask, nasal mask, mouth mask, nozzles or puffs, nasal prongs, etc, with any suitable configuration, e.g., with or without forehead support.

Also, it should be appreciated that the headgear may be used with a new patient interface or the headgear may be retrofit to an existing patient interface.

2. Manufacturing

Figure 2:
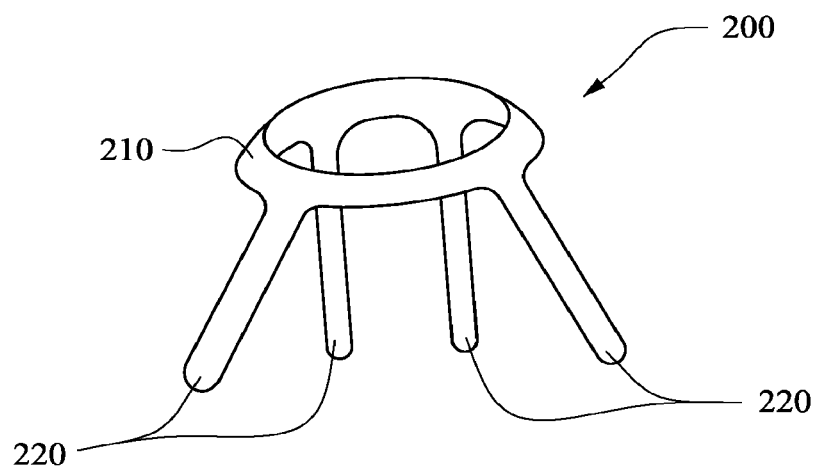
FIG. 2 is a perspective view of a headgear manufactured according to an example of the disclosed technology.

An example of a headgear 200 manufactured according to an example of the disclosed technology is shown in FIG. 2. The headgear includes a rear portion for example a "crown" or "halo" 210 and a plurality of straps 220 attached to the rear portion. The rear portion 210 is adapted to accommodate the patient's occiput and the straps 220 are configured to connect to upper and lower headgear attachment points (e.g. clips), as one skilled in the art will understand. It is noted that the headgear 200 is merely an example and that other headgear configurations may be made in accordance with the disclosed technology.

The headgear 200 is manufactured to shape (e.g., formed in one piece to shape otherwise known as "fully-fashioning" without the need to cut away any substantial amounts of material) thereby producing little or no waste material. Alternatively, the headgear may be divided into segments that are each manufactured to shape separately (e.g., by knitting) and then attached to one another. FIG. 2 demonstrates a single, unitary seamless structure having at least two regions (e.g. the rear portion 210 and straps 220), wherein the at least two regions extend from a junction (the junction being the connection between the straps 220 and the rear portion 210), where the straps extend at a different angular orientation to the rear portion. The rear portion and straps are formed in a continuous process (i.e. the material that makes up the component and the shape of the component are formed in a single step)—this is different to a process where a sheet of material is made and then cut to shape (this would not be considered a single step). FIG. 2 also shows that the straps 220 branch out or extend at a different angle or direction to the rear portion 210, without requiring seams or additional formation steps.

Figure 3:
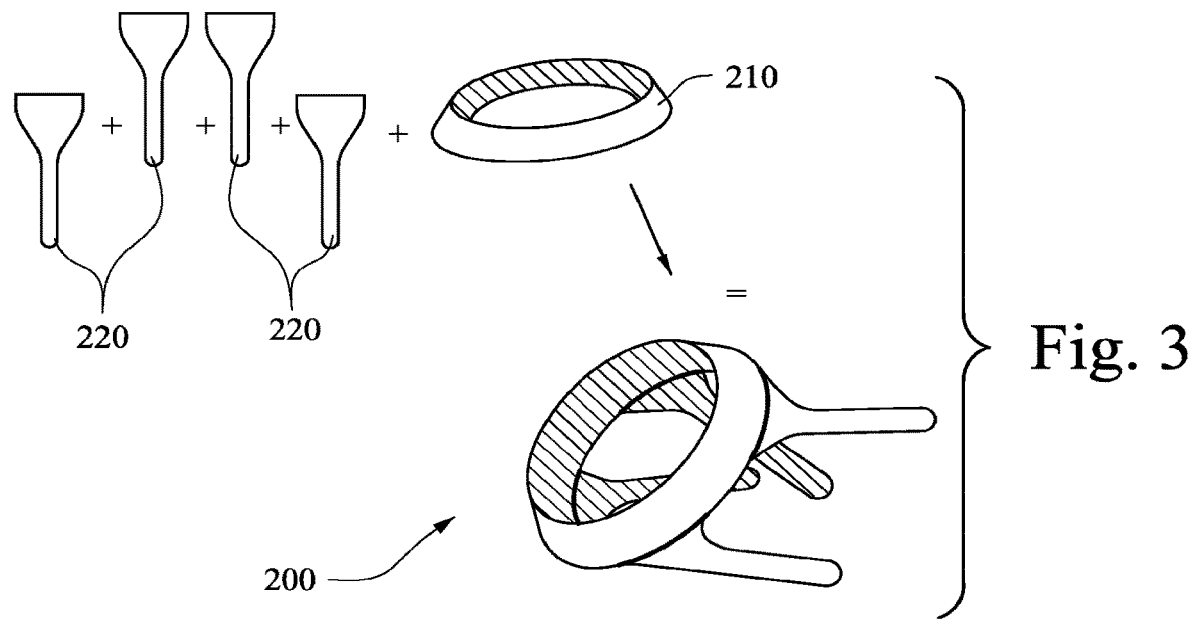
FIG. 3 shows a process of manufacturing a headgear according to another example of the disclosed technology.

In FIG. 3, the rear portion 210 and the straps 220 are formed separately and subsequently connected. One skilled in the art will understand that any portions of the headgear 200 can be formed separately and then later connected. In the example of FIG. 3, the straps 220 are stitched to the rear portion 210; however other suitable methods such as knitting, sewing, crocheting, heat bonding with adhesive tape, gluing, welding (e.g., ultrasonic welding), etc. may be used.

A knitted component such as headgear is defined as being formed of "unitary knit construction" when constructed as a one-piece knit element that is substantially free of additional stitching or bonding processes.

Figure 1:
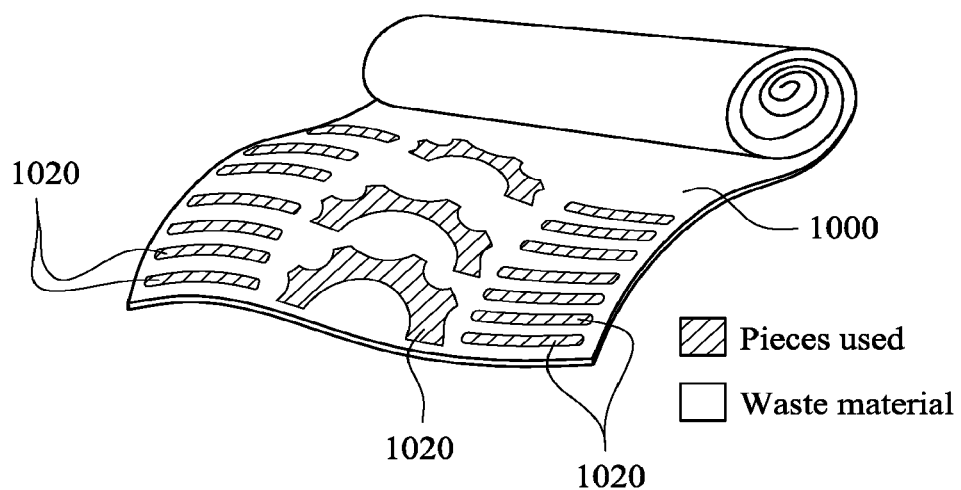
FIG. 1 shows a prior art example of headgear pieces cut from a fabric sheet.
Figures 1, 4:
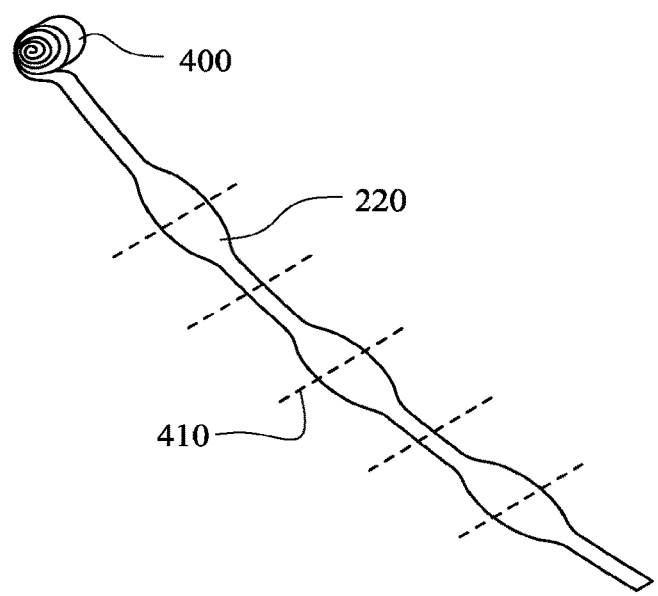
Figures 2, 4:
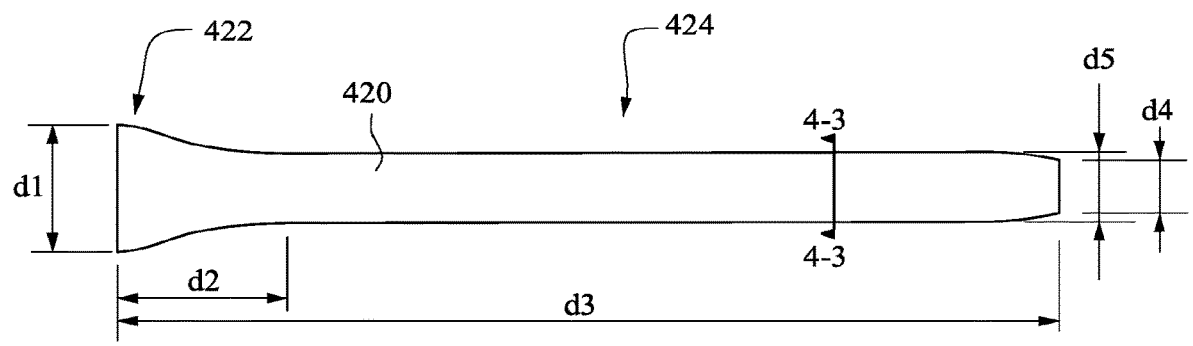
Figures 3, 4:
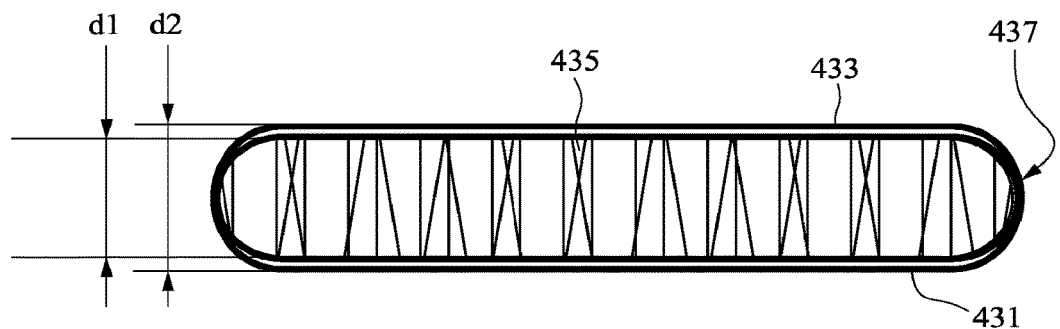
Figure 4:
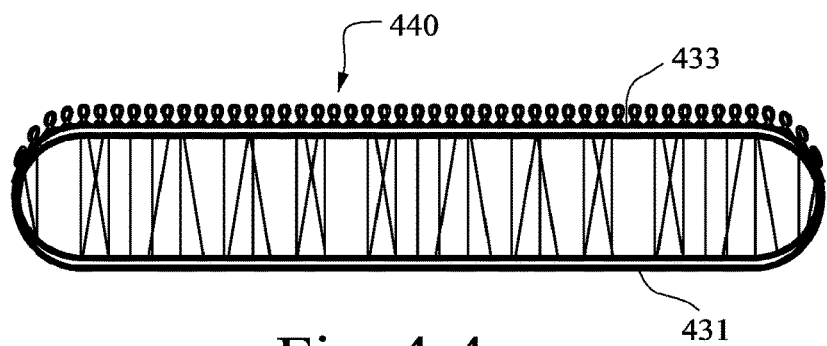

As shown in FIG. 4-1, the straps 220 may be formed (e.g., by warp knitting) as a continuous piece that is subsequently cut as this procedure may further increase manufacturing efficiency.

Knitting various headgear sections in a continuous manner may be advantageous as there are no or very few additional manufacturing steps that would be required to sew, fuse, adhere or otherwise attach adjoining sections. As a result, the manufacturing process may have reduced steps, the amount of material waste is reduced, there would be virtually no seams in the headgear between the adjoining sections, and the headgear made of a fabric without distinctive joins or seams may be more comfortable for patients.

2.1 Techniques

A number of techniques can be used in accordance with the present technology to manufacture headgear to shape with little or no waste material. Preferably, the technique may produce a headgear that is a single, unitary, seamless structure. Techniques that may produce a single unitary seamless structure include mechanical manipulation of yarn including interlooping (such as knitting), interweaving and/or intertwining (including braiding, knotting and crocheting). An alternative technique of 3D printing may also create a headgear having a unitary, seamless structure.

A manufacturing technique in accordance with the disclosed technology preferably has one or more of the following features:

1) produces little or no waste;
2) produces headgear that is comfortable for the patient;
3) produces headgear that is conformable;
4) produces headgear that is breathable;
5) produces headgear that may minimizes facial marking; and/or
6) produced headgear that is lightweight.

2.1.1 Interlooping—Knitting

In accordance with an example of the disclosed technology, headgear may be formed by interlooping such as knitting (e.g., threading yarn or thread to form a knitted fabric). The headgear may be formed by flat knitting or circular knitting, however other forms of knitting may also be possible. Flat knitting and circular knitting may be preferable as they are able to create a headgear with a unitary, seamless structure. Flat or circular knitting machines may be utilized to create a weft knit or a warp knit. A variety of knitting processes including circular knitting and warp- or weft-flat knitting, may be utilized to manufacture the headgear component or components. Flat knitting may have some advantages, including but not limited to (1) the ability to locate floating yarns within, for example, a headgear strap, in order to provide extra cushioning or bulk, and/or (2) the ability to include extra loops of yarns on either the upper or lower surface of the headgear strap, thus creating the effect of a soft terry cloth material, for example, or creating an unbroken loop fabric for engagement with a hook tape fastener, and/or (3) the ability to knit a 3D dimensional spacer fabric construction adjacent to double-faced knit construction within a single unified headgear construction.

Preferably, the headgear is formed primarily from multiple yarns that are mechanically manipulated through an interlooping process to produce a single unitary structure having various sections with different physical properties.

Figure 7:
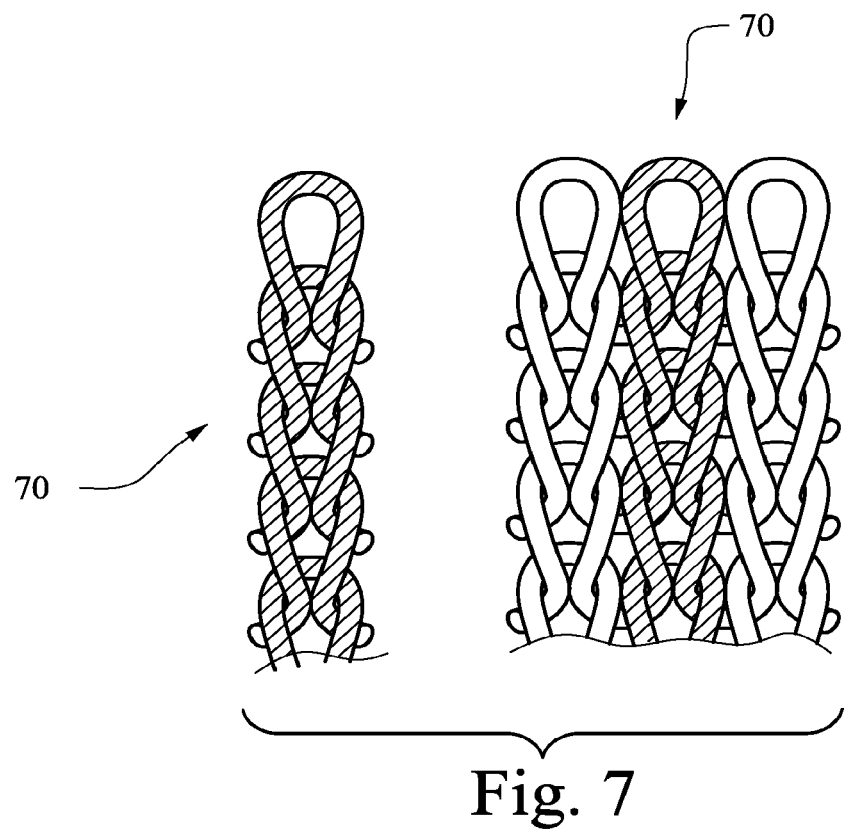
Figure 8:
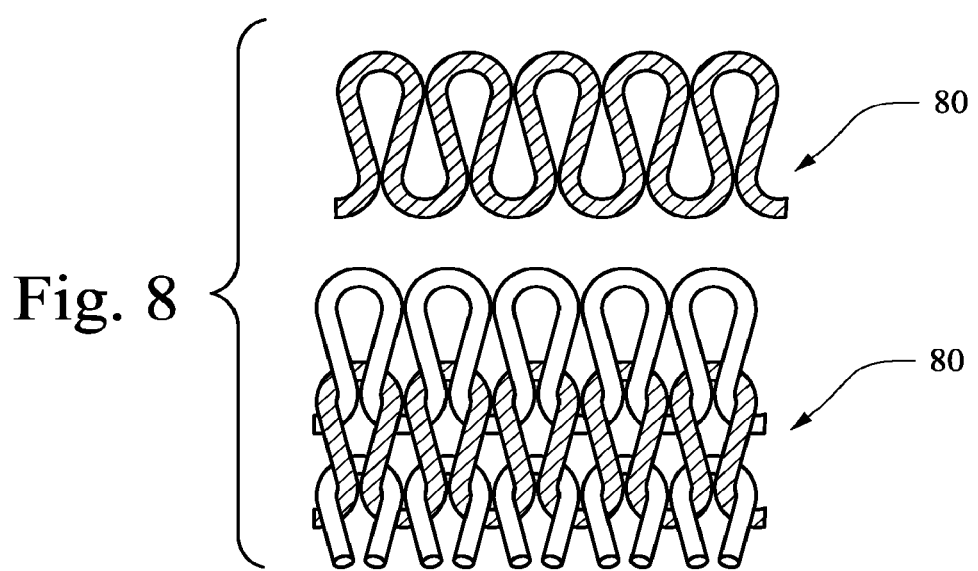
Figures 1A, 9:
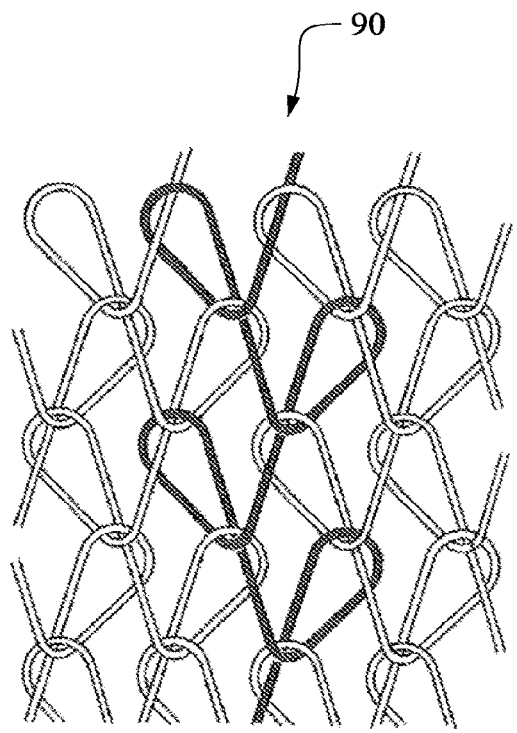
FIG. 9-1A illustrates a basic warp knitted fabric according to an example of the disclosed technology.
Figures 1B, 9:
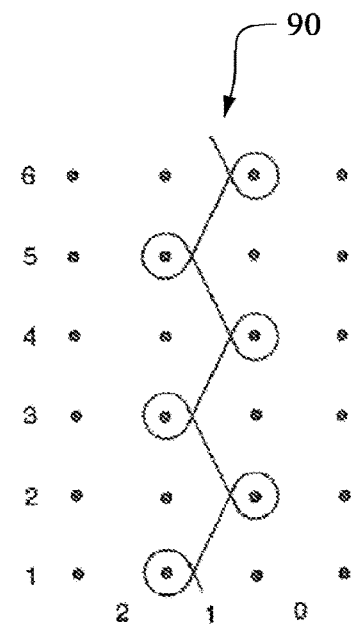
Figures 2, 9:
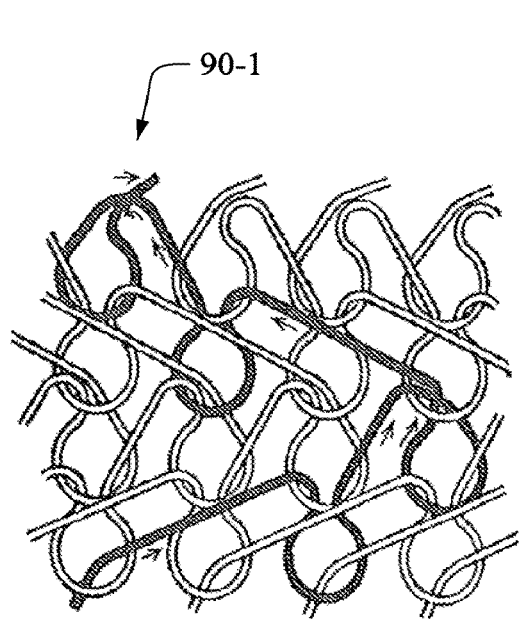
Figure 10:
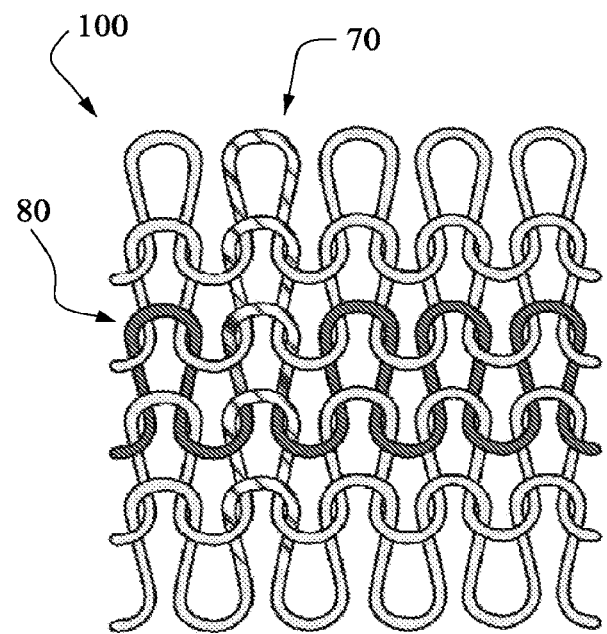
FIG. 10 illustrates a basic weft knitted fabric according to an example of the disclosed technology.

FIG. 7 illustrates the wale of a weft knit fabric 70, or the direction that the loops of one thread join to a loop of another thread. The course 80, or the direction of the loops from a single thread is shown in FIG. 8. FIGS. 9-1A and 9-1B illustrate a basic closed loop warp knit 90. FIG. 9-2 illustrates an example of a warp knit tricot jersey fabric structure in which a yarn is knitted in a vertical direction in a zig-zag manner, capturing other warp yarns, with the wale running somewhat parallel to the course.

Referring to FIGS. 9-1A, 9-1B, 9-2 and 10, a warp knit 90, 90-1 comprises the wales and courses running parallel to one another, while in a weft knit 100 the wales run perpendicular to the course. The headgear and masks of the disclosed technology may be formed by either warp knit or weft knit. A warp knit, for example tricot, raschel or locknit, is typically more resistant to runs, easy to machine, and may utilize multiple yarns (allowing for the use of multiple colors or yarn types). A weft knit can be formed with a single yarn; however, use of multiple yarns is also possible. The headgear of the disclosed technology may be constructed of a warp knit or a weft knit.

Knitted fabrics may have different stretchability characteristics compared to woven fabrics. Knitted fabrics are typically more flexible than woven fabrics, which may only stretch in one direction (depending on the yarn they are made from), and therefore may provide a more comfortable fit for the patient. Knitted textiles may be constructed in such a way that the fabric has a two-way stretch—i.e. a first yarn oriented in a first direction has a lower flexibility than a yarn oriented in a second direction. This arrangement may be desirable along the straps of the headgear such that the straps can stretch along their length but not across their width, or vice versa. Alternatively, the knitted textile may have a four-way stretch i.e. yarn in a first direction and a second direction and both are flexible such that application to a strap would allow stretch in both lengthwise and crosswise directions.

Figure 12:
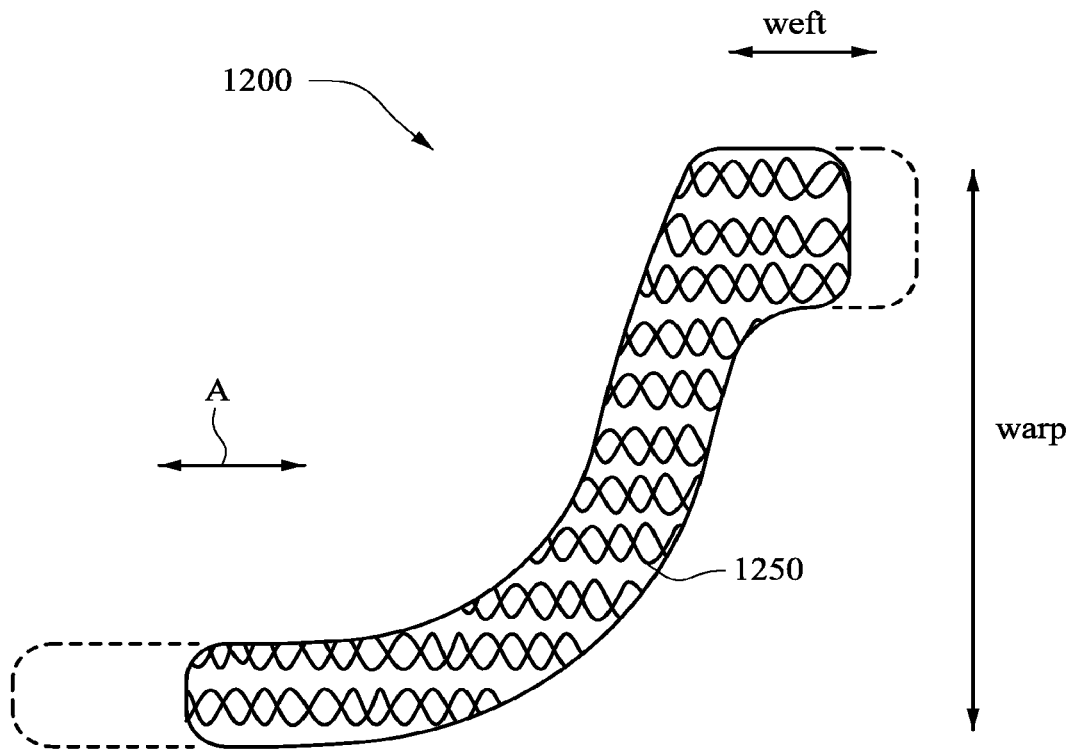
FIG. 12 illustrates an increased stretch in the direction of the course of a knitted headgear according to an example of the disclosed technology.

The example of FIG. 12 shows a strap 1200 having a grain or course 1250, and illustrates how the direction of the grain or course affects stretch. The knitted fabric will tend to stretch more readily in the direction of the course. Therefore, headgear may be designed to stretch in certain directions and be more resistant to stretch in other directions. For example, the strap 1200 will tend to stretch in its width direction A (from the patient's face to the back of the head) and may have limited stretch along the length of the strap. This configuration may increase stability of the headgear in the lengthwise direction while increasing fit range. The strap 1200 may be configured to stretch in certain directions and be resistant to stretch in other directions in order to better enable the strap 1200 to hold a mask assembly on a patient's face in a manner that enhances the seal with the patient's face.

Figures 1, 5:
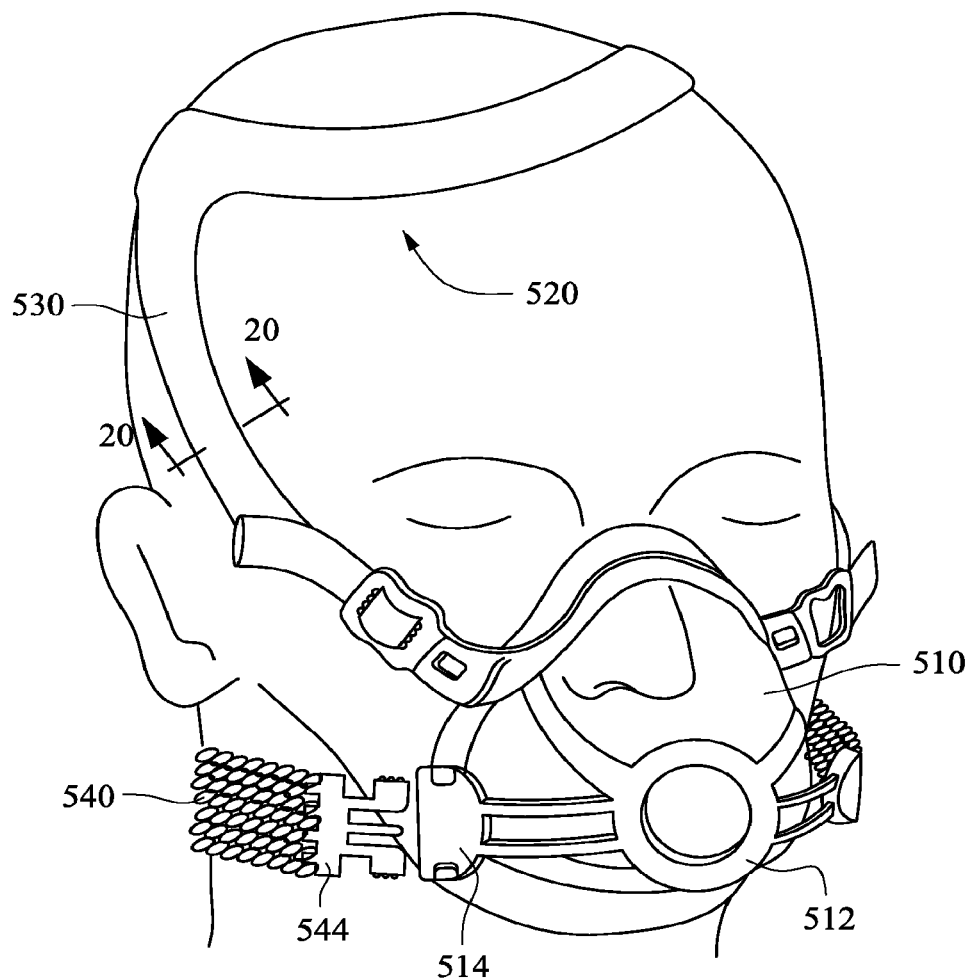
Figures 2, 5:
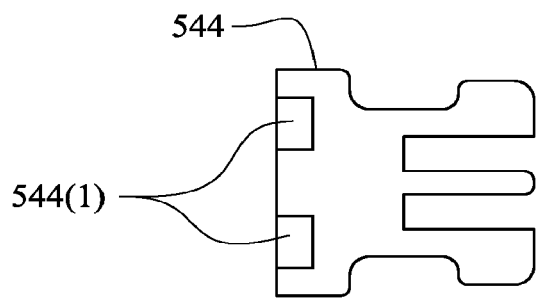

Referring to FIGS. 5-1 and 5-2, a mask 510 is held in position on a patient's face by headgear 520. The mask 510 includes an elbow coupling portion 512 adapted to connect to an elbow (not shown) for supplying pressurized air to the mask. Lower mask clips 514 are adapted to connect to the headgear 520.

The headgear 520 includes upper headgear straps 530 and lower headgear straps 540 configured for connection to the mask 510. An attachment member 544 (e.g., a lower headgear clip) may have connecting portions 544(1) (e.g., holes) for receiving the strap material (e.g., thread or yarn). For example, yarn comprising the lower headgear strap may be looped through the holes 544(1) during fabrication of the strap to integrate the clip 544 and the strap 540.

Figure 6:
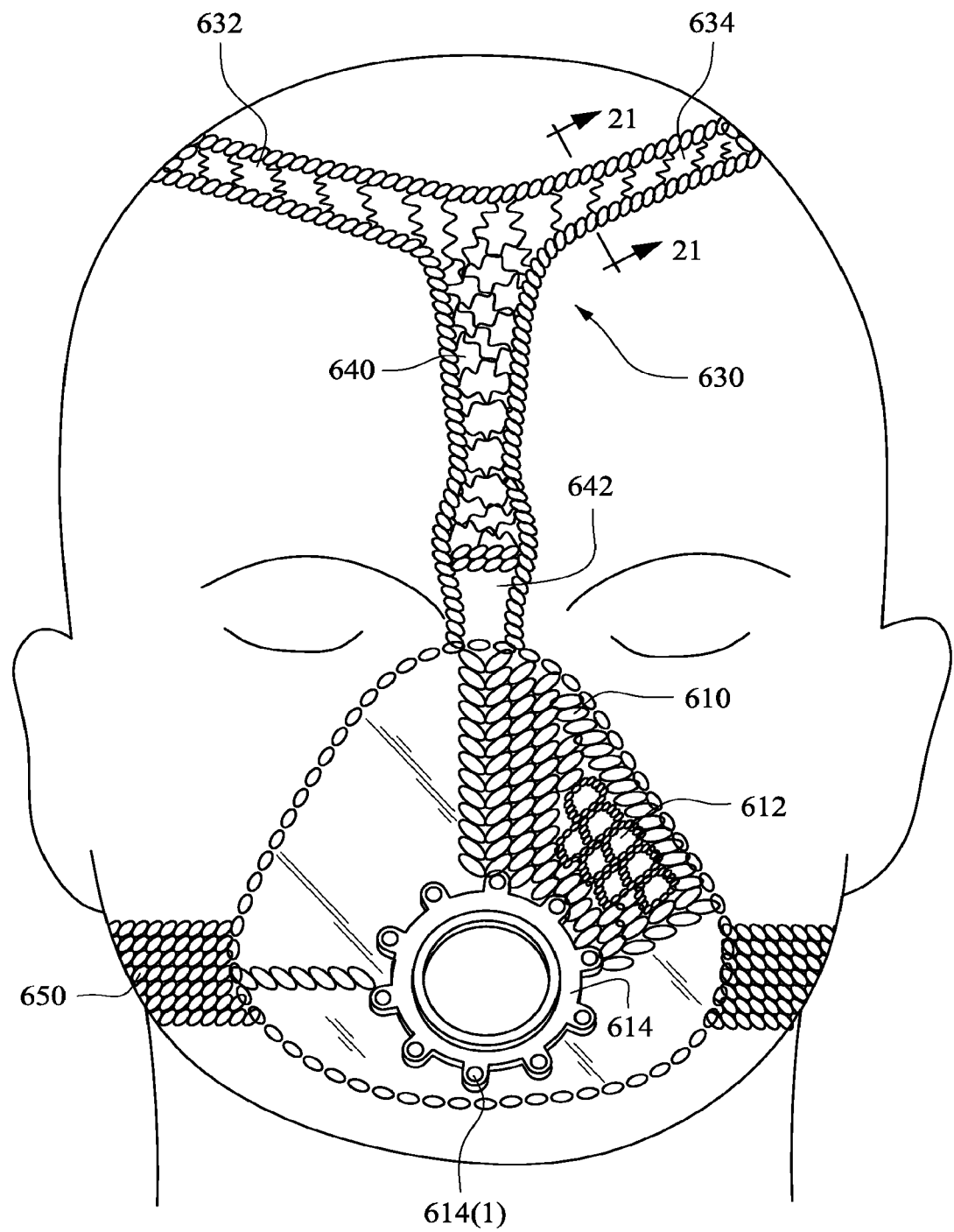

In an alternative example shown in FIG. 6, a mask 610 and headgear 630 are integrally formed as one piece. The mask 610 is knit to include open areas which function as vent holes 612. An elbow coupling portion 614 includes holes 614(1) for receiving the yarn or thread thereby integrating the mask 610 and elbow coupling portion 614. The mask may be made air tight by laminating or other suitable methods.

The headgear 630 includes crown straps 632, 634, top strap 640, and lower headgear straps 650. The knit may be pulled tight or formed loosely to adjust the fit and enhance comfort in certain areas. For example, the illustrated crown straps 632, 634 have a looser knit which enhances breathability in the area near the top of the patient's head. In contrast, the lower headgear straps 650 have a tight knit which creates a more rigid strap for stabilizing the mask. The top strap 640 includes a thinned region 642 designed to avoid obstruction of the patient's vision.

Figure 11:
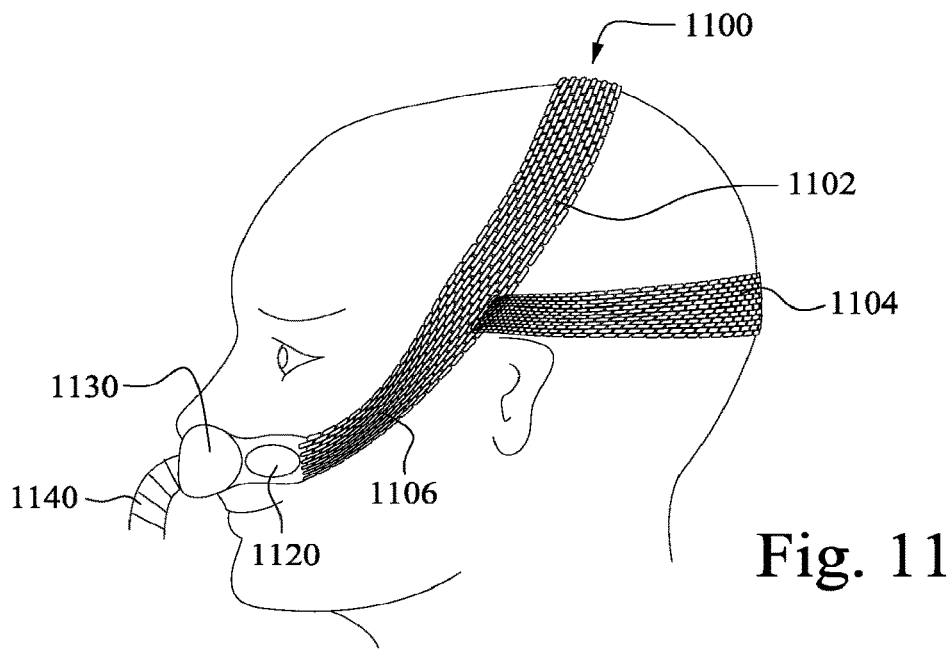
FIG. 11 is a side view of headgear positioned on a patient's head in accordance with an example of the disclosed technology.
Figure 11A:
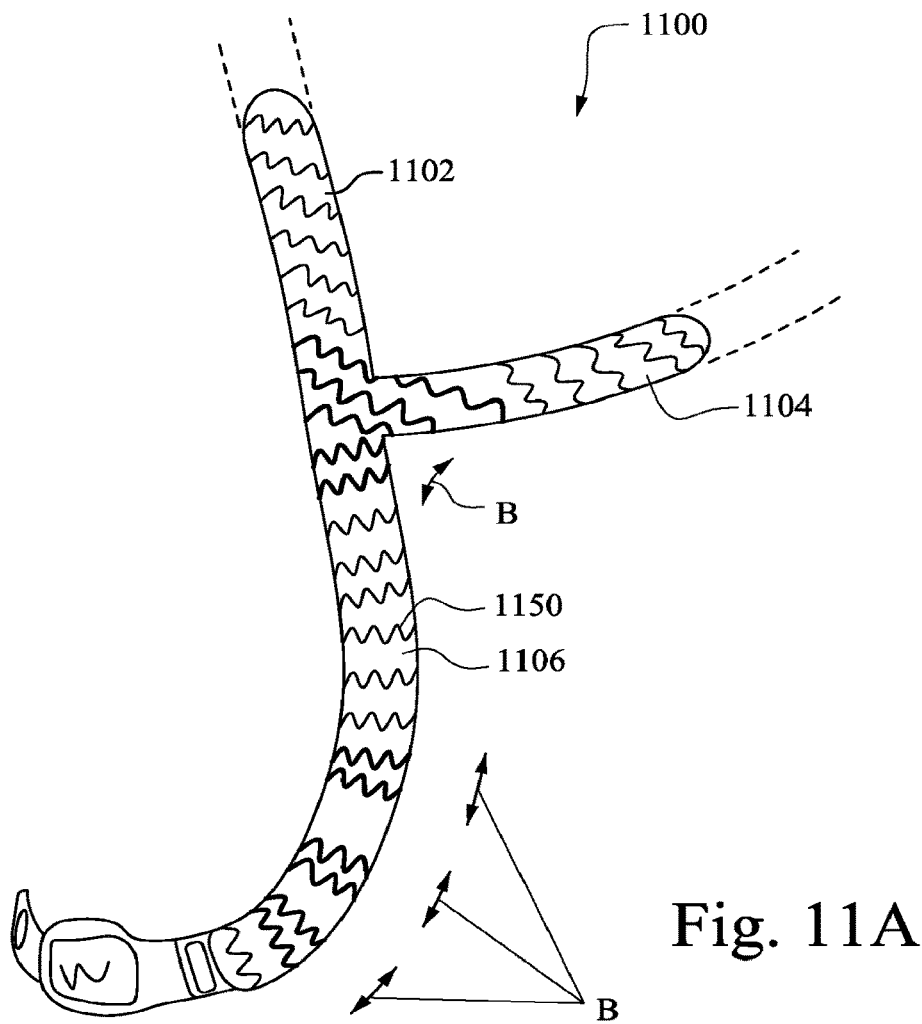
FIG. 11A shows the changing direction of the course or grain of the headgear of FIG. 11 according to an example of the disclosed technology.

Referring to FIGS. 11 and 11A, a knitted strap 1100 includes a top portion 1102, a rear portion 1104, and a lower portion 1106. The lower portion 1106 may bifurcate or branch out at a junction to form the top portion 1102 and the rear portion 1104. The angular orientation of the top portion 1102 may be different compared to the rear portion 1104 e.g. the top portion 1102 may extend at about 30-110 degrees, or about 90 degrees or perpendicular to the rear portion 1104. The direction of the knit, or the grain or course 1150 of the knit, may be altered to adjust the shape or stretch of the fabric in certain areas. For example, the grain or course 1150 may be configured to curve the strap at a cheek region to avoid obstructing the patient's eyes. Further, as shown in FIG. 11A, the grain or course 1150 may curve, as shown by the arrows B, to a split thereby forming the top portion 1102 and the rear portion 1101. Such configurations of the top portion 1102 and the rear portion 1101 may stabilize the straps in position on the patient's head and thus better enable the strap 1100 to hold a mask assembly on a patient's face in a manner that enhances the seal with the patient's face.

The strap 1100 may support a patient interface 1130 (e.g., a nasal mask) on the patient's face. A connector 1120 may be used to attach the strap 1100 to the patient interface 1130, and a supply tube 1140 may deliver breathable gas to the patient's airways via the patient interface. In the illustrated example, the patient interface 1130 is positioned under the patient's nose and seals against the external surfaces of the patient's nose.

The headgear of the disclosed technology may further comprise a pocket, tunnel, layers and/or ribs. Such structures may be formed in one piece by circular or flat knitting. The pockets or tunnels may be reinforced with materials having a higher stiffness or rigidity than the knitted textile, thereby rigidizing the headgear. Rigidizing the headgear may better stabilize the mask in position on the user's face. Materials used for rigidizing the headgear may include plastics such as nylon, polypropylene, polycarbonate, or higher stiffness textiles such as braided ropes. Preferably, the rigidizing of the headgear may be positioned at boney regions of the patient's head, for example the cheeks, occiput or crown. The reinforcing structure may be inserted during the knitting process, for example, a stiffer or flatter yarn or a rigid polymer element may be inserted into the knit construction, during or after the knitting process. The strands or rigid components would function to withstand tension and bear the stresses e.g., due to tightening of the headgear straps for therapy, or to stabilise the mask better, or would assist to act as coupling or fastening agents to attach the headgear piece(s) to the mask interface.

Alternatively, the pockets or tunnels may be cushioned to add comfort. For example, pockets or tunnels may be filled with foam, gel, floating yarn, looped yarn or other cushioning material.

Preferably, the headgear is formed by flat knitting or circular knitting, wherein the headgear has selvedges. That is, the headgear may be formed to have a finished configuration such that the ends of the yarns used to construct the headgear are substantially absent from the edges of the headgear components. An advantage of fashioning the headgear components to the finished shape is that the yarns are not being cut, and are thus less likely to unravel and may require fewer finishing steps. By forming finished edges, the integrity of the headgear is maintained or even strengthened and fewer or no post-processing steps are required to either (1) prevent unravelling of the headgear component and/or (2) create an edge that is distinct yet soft (such as in ultrasonically cutting and sealing a 'soft edge' on a fabric-foam-fabric laminate material) and/or (3) enhance the aesthetic and durability characteristics of the headgear.

The headgear of the disclosed technology may be formed by a regular or irregular pique knit. A pique knit will orient a first yarn on the right side (non-patient contacting side that is visible once headgear is donned) and a second yarn on the wrong side (the patient contacting side that is not visible once the headgear is donned). That is, the yarn exposed on the right side may be different to the yarn exposed on the wrong side. For example, the yarn on the right side may have a pleasant visual appearance and the yarn on the wrong side may have a nice hand feel for contacting the patient's skin. Alternatively, or in addition, the yarn on the right side may have a first moisture wicking property and the wrong side may have a second moisture wicking property. For example, the yarn on the right side may have a high percentage of microfiber having a first moisture wicking property and the wrong side may have a high percentage of non-microfiber having a second moisture wicking property.

The headgear may be preferably formed as a unitary knit structure which may also be uniform in material and properties, for simplicity, but preferably it will be formed as a unitary structure including various sections that have different physical properties, joined in a seamless manner. The various sections may exhibit, for example but not limited to, different degrees of strength, abrasion resistance, wear resistance, flexibility, enhanced durability, higher or lower moisture absorption (moisture absorbability), moisture-wicking ability, water affinity, breathability or air-permeability, liquid permeability, stretch or stretch-resistance, compressibility, cushioning ability, support, stiffness, recovery, fit, and form. The various sections may be constructed to exhibit variations in directional stretch, such as four-way stretch, or bi-directional stretch, a tailored level of stretch resistance, or no stretch. This may be achieved by, for example but not limited to, selecting a particular yarn or knit construction type.

The headgear as a unified seamless structure may be formed in one piece with uniform characteristics, or from two or more sections with varying characteristics. The two or more headgear sections may differ by way of using two or more different yarns of different twist, denier, fibre composition, etc., thus imparting different physical properties to the headgear structure. The two or more headgear sections may differ by way of using two or more various knit stitch types, thus imparting unique physical properties to the two sections.

Whereas one region may incorporate, for example, elastane or PBT (Polybutylene terephthalate polyester) to enhance stretch, the other region may incorporate, for example, nylon or polyester to enhance durability. Similarly, while one region of the headgear may incorporate yarn with one denier, the other region may include a yarn with a greater or reduced denier, crimp or texture, in order to customize the cushioning, thickness or bulk.

The two or more sections within a headgear construction may be connected by using tuck stitches or other knit stitches that, for example, join a first section to a second section in a seamless manner. This would be achieved by knitting the first section, then knitting the tuck stitches between the first knitted section and a second knitted section, then knitting the second section. The tuck stitches are utilized to seamlessly connect sections between wales, especially when using a narrow-tube circular knitting machine.

The headgear piece may be finished without a seam. If it is made with an un-dyed yarn, this may be achieved by finishing the knitting process with a yarn that contains water-soluble fibres. The water-soluble fibers permit the fabric to shrink in the dyeing process and provides a neatly-finished edge, eliminating the need to create an additional seam on the edge.

In order to enhance manufacturing efficiency, knitting machines may also be utilized to form a series of joined headgear components, such as straps or crown components. That is, the knitting machines may form a single component that includes a plurality of headgear pieces. Each of the headgear segments may have substantially identical shapes and sizes. Alternatively, each of the headgear pieces may even have different shapes and sizes, which may be programmed in sequence. Moreover, a knit release area (which may consist of, for example but not limited to, dissolvable yarns, loosely knitted yarns, finer denier yarns or easy-to-tear placeholder yarns) may be knitted into the series of headgear components in order to allow the various headgear parts, for example, straps, to be separated without the need for cutting operations.

2.1.1.1 Spacer Fabric

In an example of the disclosed technology, headgear may be formed using spacer fabric material. A spacer fabric can be defined as a textile having an upper ground structure or layer, a lower ground structure or layer, and a floating or traversing yarn woven between the upper ground structure and lower ground structure to form a matrix like textile. The upper ground structure and lower ground structure may be formed from a fabric. The upper ground structure may have different properties to the lower ground structure, for example they may have different stretch, stiffness, flexibility, hand feel, or other characteristics. The upper and lower ground structures may be substantially parallel to one another. Spacer fabrics may be formed by flat knitting. At least one side (i.e. upper or lower ground structure) may be formed from a fabric having yarn of, for example, about 30-100 denier, 20-300 denier, or 50-200 denier for a pleasant hand feel.

Figure 13:
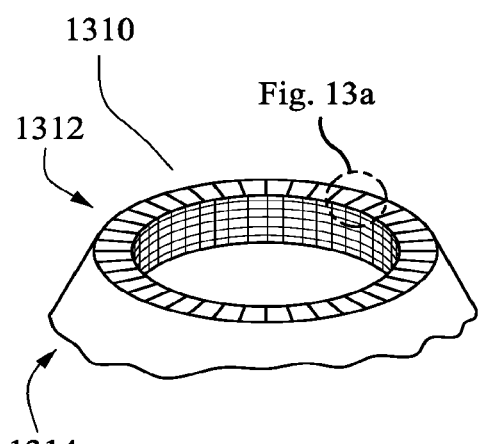
FIGS. 13 and 13a show headgear according to an example of the disclosed technology.
Figure 13A:
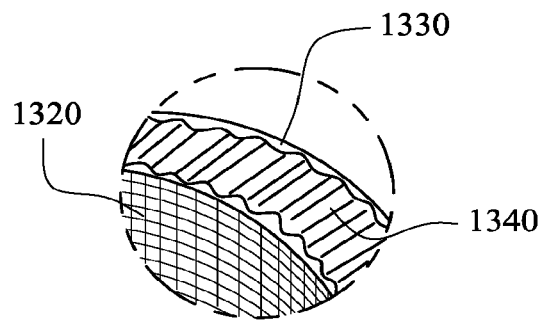

In the example of FIGS. 13 and 13a, a rear portion 1310 includes an inner fabric 1320 for interfacing with a patient, an outer fabric 1330, and spacer threads 1340 joining the inner and outer fabrics. The inner fabric 1320 may be configured to be soft and capable of wicking moisture in order to enhance comfort. The outer fabric may be designed to have a low friction surface so as to enable movement while sleeping without disrupting the position of the mask. The outer fabric may also have an anti-soil surface and may further include unbroken loop to facilitate attachment of straps.

Figures 1, 14:
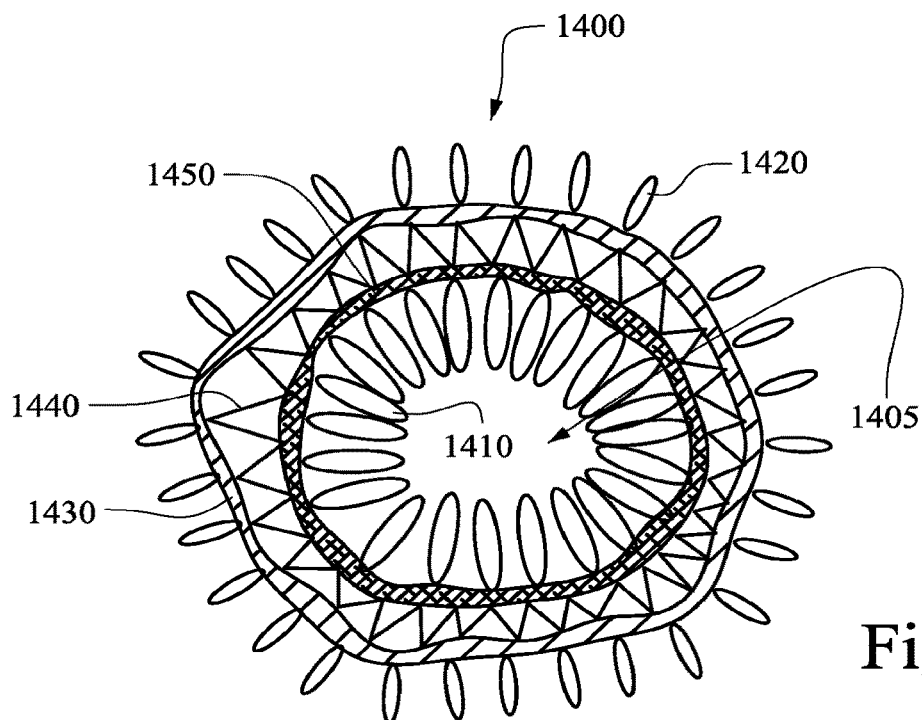
Figures 3, 14:
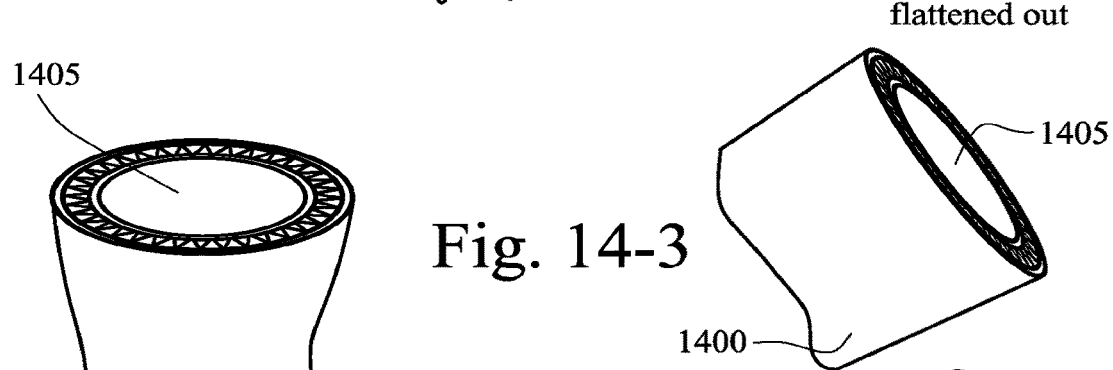
Figures 2, 14:
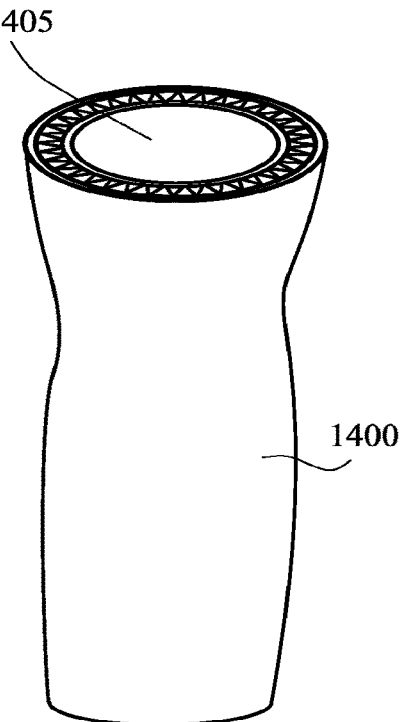
Figures 4, 14:
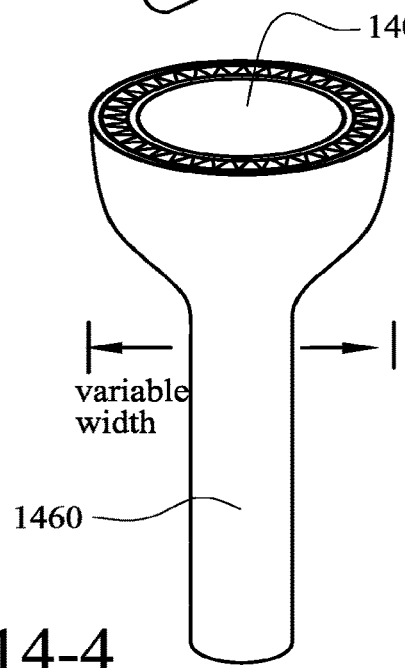
Figures 5, 14:
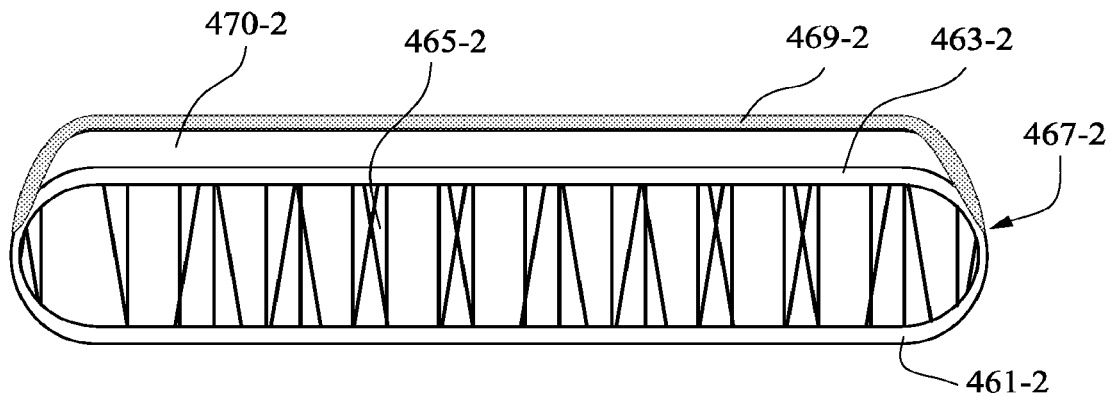
Figures 6, 14:
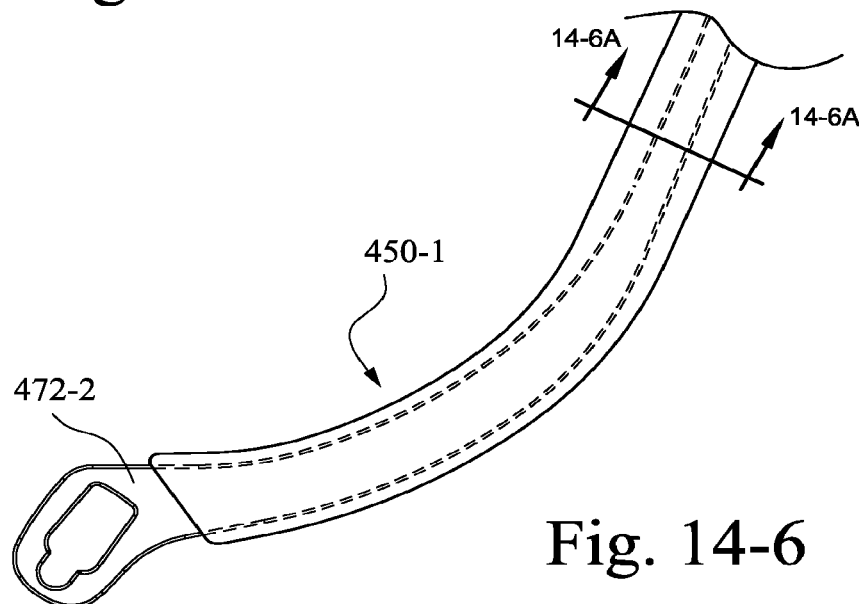

In another example, headgear may be formed as a knitted tube having an inner space 1405, as shown in FIGS. 14-1 to 14-4. A tubular headgear piece 1400 includes an outer fiber/interfacing fabric 1430, an inner spacer fiber or pile (connecting layer) 1440, and an inner fiber/fabric 1450. The tubular piece 1400 is constructed by a device having inner and outer needles 1410,1420 which may be programmed to knit the outer fiber/interfacing fabric 1430, the inner spacer fiber, and the inner fiber/fabric 1450.

The tubular piece 1400 may flatten out in use, when under tension, to form a low profile headgear piece (e.g., a strap), as shown in FIG. 14-3. Further, referring to FIG. 14-4, a tubular strap 1460 may have a varying diameter such that a portion connecting to the rear portion 1310 is wider than the ends adapted to connect to the mask. This configuration may reduce the visual obtrusiveness of the headgear strap 1460.

In another example, the inner space 1405 may be configured to transit air, thus forming an air delivery conduit. PCT Application PCT/AU2012/000667, filed Jun. 8, 2012, describes air delivery conduits that are made of textile or fabric materials. This application is incorporated herein by reference in its entirety. Such air delivery conduits described in the PCT/AU2012/000667 application may be manufactured to shape (or fully-fashioned) as described according to any of the examples described in this application, and further may be implemented into any of the examples described in this application.

Turning to FIGS. 15-1 and 15-2, the depth or thickness of the headgear may be varied by altering the length of the spacer yarns (spacer threads). A headgear piece 1500 includes an inner fabric 1520, an outer fabric 1525, and spacer threads 1540. The headgear piece 1500 may include thinner regions 1510 and thicker regions 1520. In the example of FIG. 15-1, a gradual transition between the thinner regions 1510 and the thicker regions 1520 is formed. In contrast, a steeper transition can be seen in the example of FIG. 15-2. One benefit of a tailored cushion with differing thicknesses might be cushioning which changes in thickness to correspond to certain facial bone/muscle structure creating contour, comfort and padding, or thinner zones for breathability and temperature management.

Referring to FIGS. 15-3 to 15-5, the thickness of a strap 1530 can also be varied to create rigid portions 1532 and connecting portions 1534. The rigid portions 1532 may function as rigidizers or stabilizers and provide form in certain areas of the headgear. The connecting portions 1534 may include a hole or other structure utilized to connect the strap 1530 to a mask.

Figure 16:
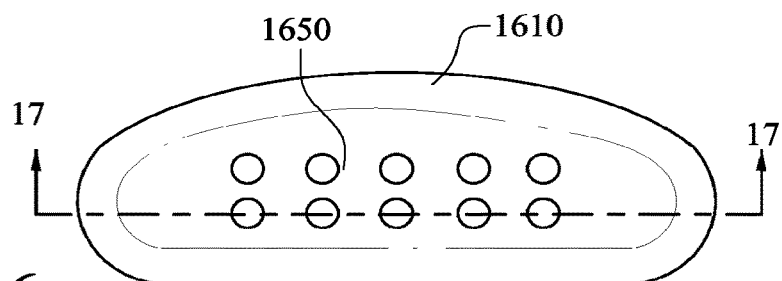
FIG. 16 is a front view of a mask which may or may not include a vent component according to an example of the disclosed technology.
Figure 17:
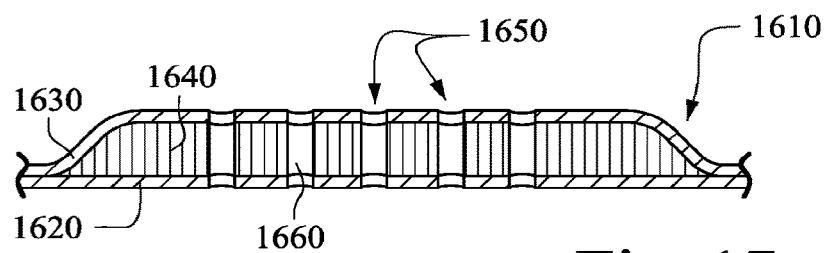
FIG. 17 is a cross-sectional view along the line 17-17 of FIG. 16.

In addition to varying the depth or thickness of the headgear, gaps may be formed in the spacer threads. These gaps may be utilized to form vent holes in a mask or create flexible areas of the headgear, for example. In FIGS. 16 and 17, a mask 1610 includes an inner fabric 1620, an outer fabric 1630, and spacer threads 1640. Voids 1660 in the spacer thread may be used to create vent holes 1650 in the mask. To facilitate this feature, the inner 1620 and outer 1630 fabrics are thinned in the areas of the voids 1660. Ends of the mask may be welded, knit, or joined in any other suitable manner.

Figure 18:
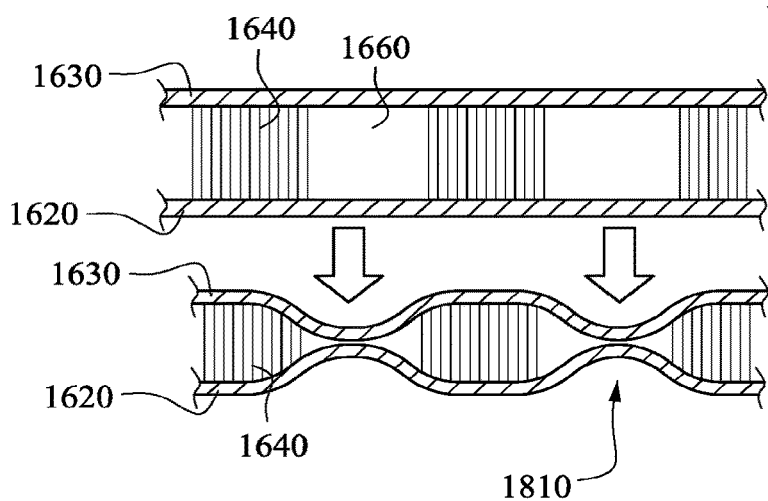
FIG. 18 is a cross-sectional view of a headgear piece having thinned regions according to an example of the disclosed technology.
Figure 19:
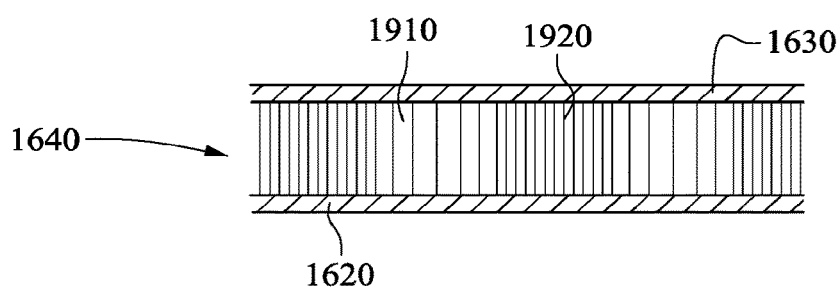
FIG. 19 is a cross-sectional view of a headgear piece having more dense and less dense regions according to an example of the disclosed technology.

Alternatively, the voids 1660 may be thermoformed or otherwise compressed to form thinned regions 1810, as shown in FIG. 18. The thinned regions 1810 may form hinges or areas adapted to bend the headgear around a curve (e.g., around the patient's occiput).

In a further example, the spacer threads 1640 may be unevenly spaced to create less dense areas 1910 and more dense areas 1920. These areas may permit flexibility of the headgear to be adjusted as desired. For example, the headgear may be stiffer (dense area 1920) at the cheek bone region and flexible (less dense 1910) at the cheek muscle region.

Figure 20:
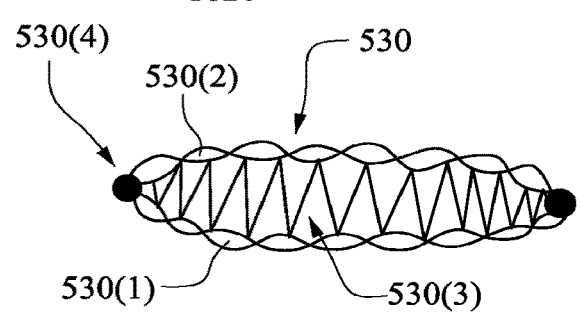
FIG. 20 is a cross-sectional view along the line 20-20 of FIG. 5-1.
Figure 21:
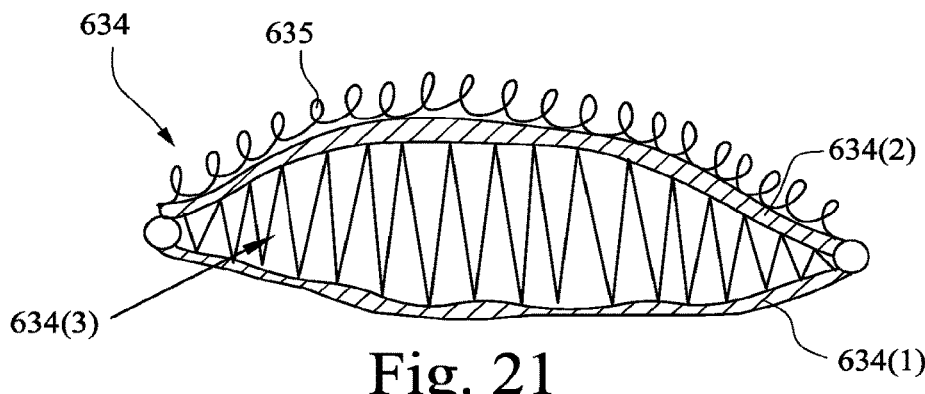
FIG. 21 is a cross-sectional view along the line 21-21 of FIG. 6.

In alternative examples, the headgear 520 and the headgear 630 of FIGS. 5-1 and 6 may include spacer material, as shown in the cross-sectional views of FIGS. 20 and 21. The spacer fabric construction may provide more cushioning, breathability, moisture management (e.g. moisture absorbability or wicking), and/or desirability (e.g., comfort and/or aesthetic appeal).

Referring to FIG. 20, the upper headgear strap 530 may include an inner fabric 530(1), an outer fabric 530(2), and spacer yarns. 530(3). Further, the edge of the strap 530 may be knitted to draw the outer fabric 530(2) into engagement with the inner fabric 530(1) to create an integrated seamless edge 530(4). Alternatively, the inner and outer fabrics may be welded (e.g., ultrasonic welded) at the edge of the strap 530.

Referring now to FIG. 21, the crown strap 634 may include an inner fabric 634(1), an outer fabric 634(2), and spacer yarns 634(3). Additionally, the outer fabric 634(2) may be brushed or otherwise treated to form unbroken loop material for receiving hook material.

Alternatively, the headgear may be constructed by braiding, crocheting, a net construction or raschel pattern, a single layer knit or a double layer knit such as an interlock or jersey, or even via additive manufacture (3D printing). In the case of a basic single face fabric or double face knit, it may be preferable to use a textured yarn which may provide appropriate cushioning and bulk, to enhance comfort to the patient.

Referring to FIGS. 4-2 to 4-4, a warp knitted strap 420 formed of spacer fabric is shown. The strap 420 includes an inner fabric 431, an outer fabric 433, and spacer yarns 435. The strap may be formed of nylon and/or polyester, or any other suitable materials. The inner fabric 431 and the outer fabric 433 may have a soft surface having a high density. The strap may have a wider portion 422 adapted to connect to another headgear member (e.g., a rear portion) and a thinner portion 424 adapted to connect to a mask. The spacer yarns or pile may be formed to be shear resistant. The inner and outer fabrics are knitted together at the selvedges 437 to enclose the spacer pile. In another example, as shown in FIG. 4-4, the outer fabric 433 includes unbroken loop material 440 for receiving hook material.

In an example, as shown in FIG. 4-2, d1 may be about 22.5-42.5 mm, e.g., 32.5 mm, d2 may be about 30-50 mm, e.g., 40 mm, d3 may be about 152-292 mm, e.g., 222 mm, d4 may be about 11-17 mm, e.g., 14 mm, and d5 may be 14-22 mm, e.g., 18 mm. Further, as shown in FIG. 4-3, d1 may be about 1.75-3.25 mm, e.g., 2.5 mm and d2 may be about 2.25-3.75 mm, e.g., 3 mm.

In FIGS. 4-5 to 4-9, a warp knitted strap 450 includes an inner fabric 461, an outer fabric 463, and spacer yarns 465. In contrast to the strap 420 above, the strap 450 has a constant width. The spacer yarns or pile may be formed to be shear resistant. The inner and outer fabrics are knitted together at the selvedges 467 to enclose the spacer pile. In another example, as shown in FIG. 4-7, the outer fabric 463 includes unbroken loop material 470 for receiving hook material. In a further example the outer fabric 463 may be elasticated to form a high-tension outer fabric 463-1, as shown in FIG. 4-8. The elasticated outer fabric 463-1 pulls the selvedges 467 to the outer surface of the strap, and may function to cause the headgear strap to curl upwards and inwards towards the outer fabric layer of the strap. In cross section, as shown in FIG. 4-8, the strap may have the appearance of the letter C. This arrangement may be advantageous in reducing facial marking as the strap does not have a distinct edge when pressed against the patient's skin, since the edge curls up away from the skin.

In an example, as shown in FIGS. 4-5 and 4-6, d1 may be about 1.75-3.25 mm, e.g., 2.5 mm, d2 may be about 2.25-3.75 mm, e.g., 3 mm, and d3 may be about 11-17 mm, e.g., 14 mm.

2.1.1.2 Double Knit or Interlock

Figures 1, 22:
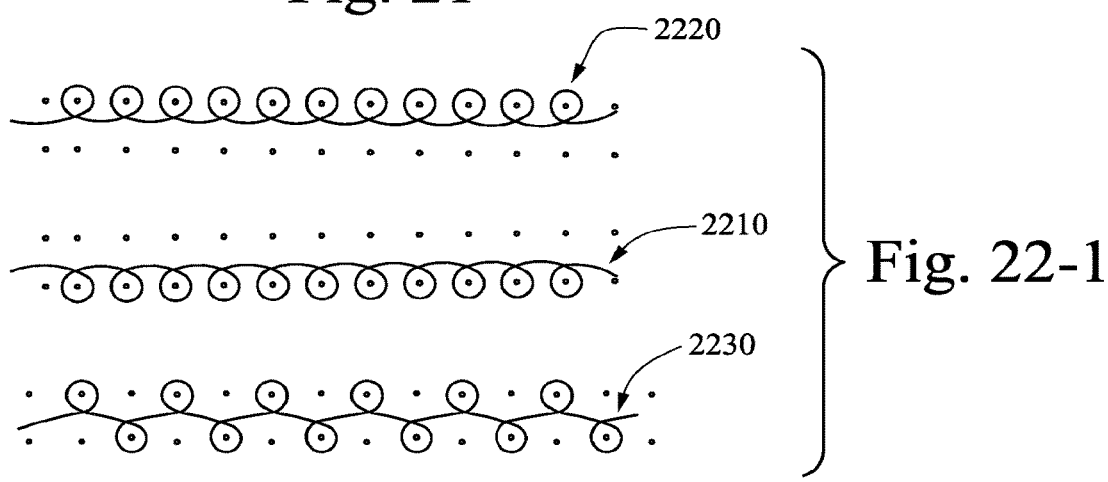
Figures 2A, 22:
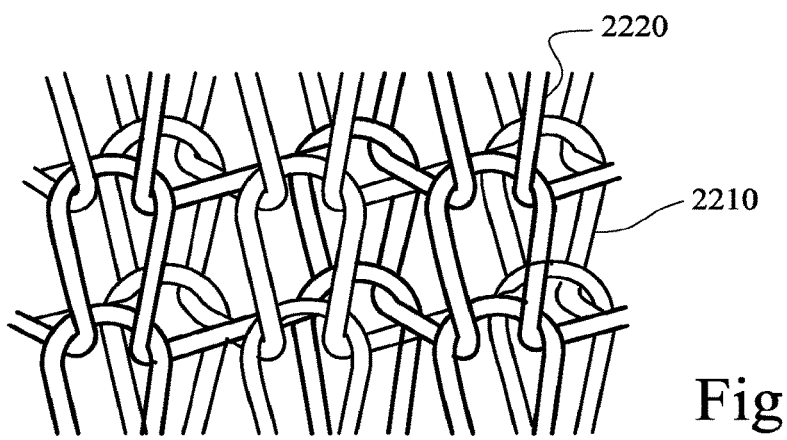
Figures 2B, 22:
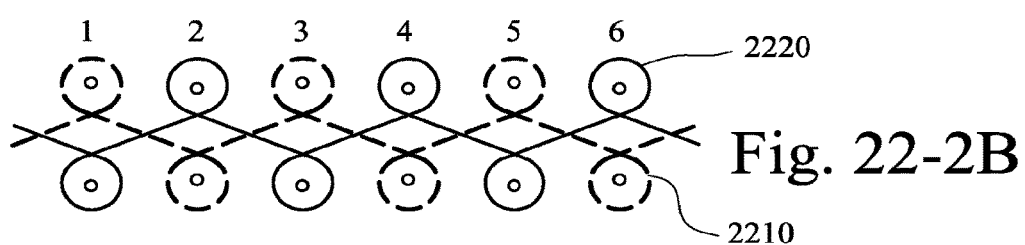

Alternatively, in accordance with another example, headgear may be formed to shape having an inner and outer face with no space in between these faces. FIG. 22-1 is a schematic representation of a double knit and FIGS. 22-2A and 22-2B illustrate an interlock knit. In FIGS. 22-1, 22-2A and 22-2B, an inner fabric 2210 and an outer fabric 2220 are knitted in such close proximity that they form a double-faced fabric such as interlock, double knit or double jersey. As shown in FIG. 22-1, the inner 2210 and outer 2220 fabrics are knitted at the same time with a spacer yarn 2230 that pulls the inner 2210 and outer 2220 fabric layers together. However, in the example of FIGS. 22-2A and 22-2B, the inner 2210 and outer 2220 fabrics are knitted concurrently (at the same time) without the need for an additional spacer yarn in a manner commonly known as interlock, whereby there are two sets of yarns which form the inner and outer fabric respectively.

Double faced or knit fabrics may be beneficial for use in headgear as the fabric may be flatter (i.e. thinner in fabric thickness, not thinner in strap width) than most conventional headgear materials (e.g. foam laminate) so as to be as unobtrusive as possible for the patient, but more substantial, dense, durable, robust or stiff than a single-knit. A double knit fabric may also permit a first characteristic or pattern/structure on one side of the fabric with a second characteristic or pattern/structure on the opposite side of the fabric. For example, a soft yarn may be provided on the patient contacting side, and a more durable yarn or construction on the non-patient contacting side. In a further example, a wicking microfiber may be provided on the patient contacting side and a hydrophilic material may be provided on the non-patient contacting side. In a further example a cotton yarn may be provided on the patient contacting side and a polyester outer may be provided on the non-patient contacting side. A double knit fabric may be preferable to a spacer fabric as the double knit may be less expensive and less complex due to the smaller number of layers.

2.1.1.3 Stitching

Figure 23:
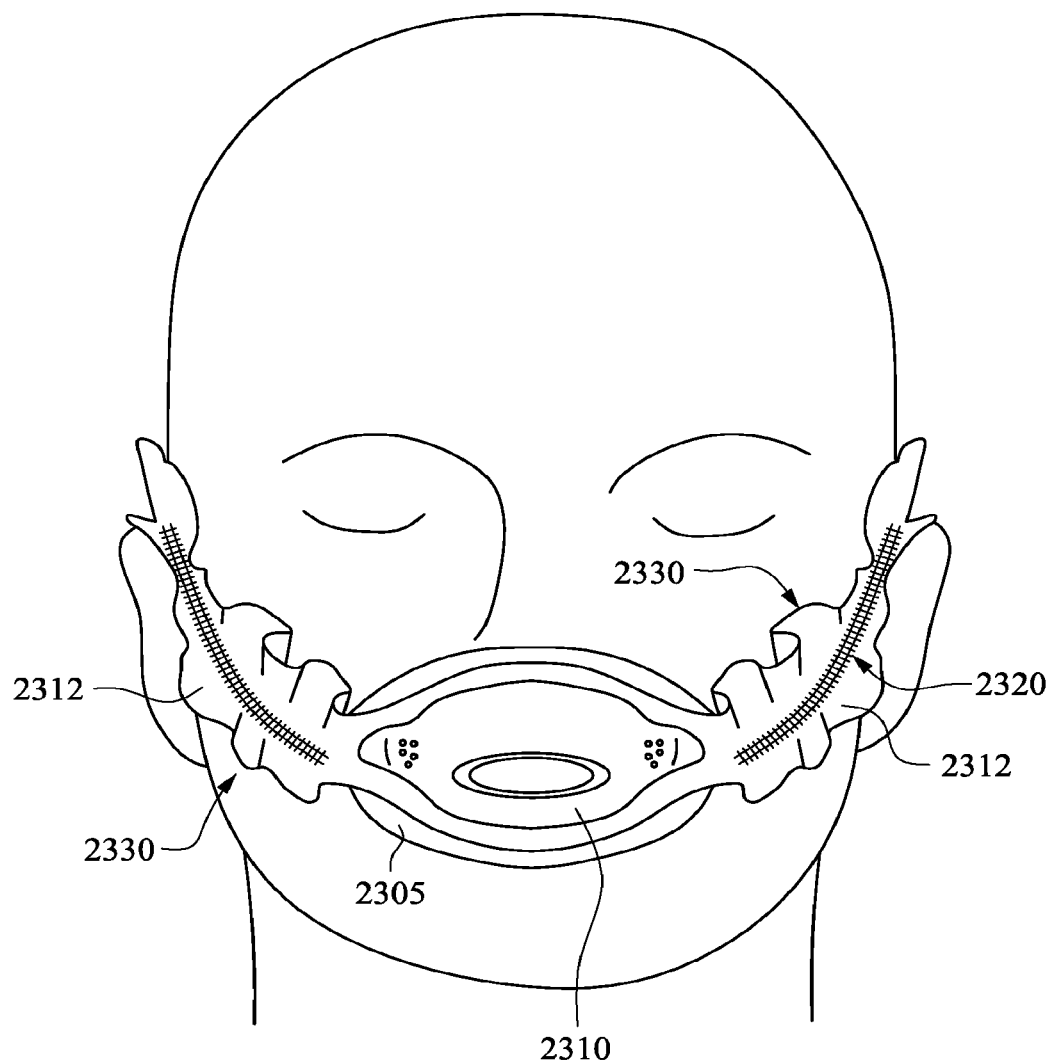
FIG. 23 is a front view of headgear and a mask in position on a patient's head according to an example of the disclosed technology.
Figure 24:
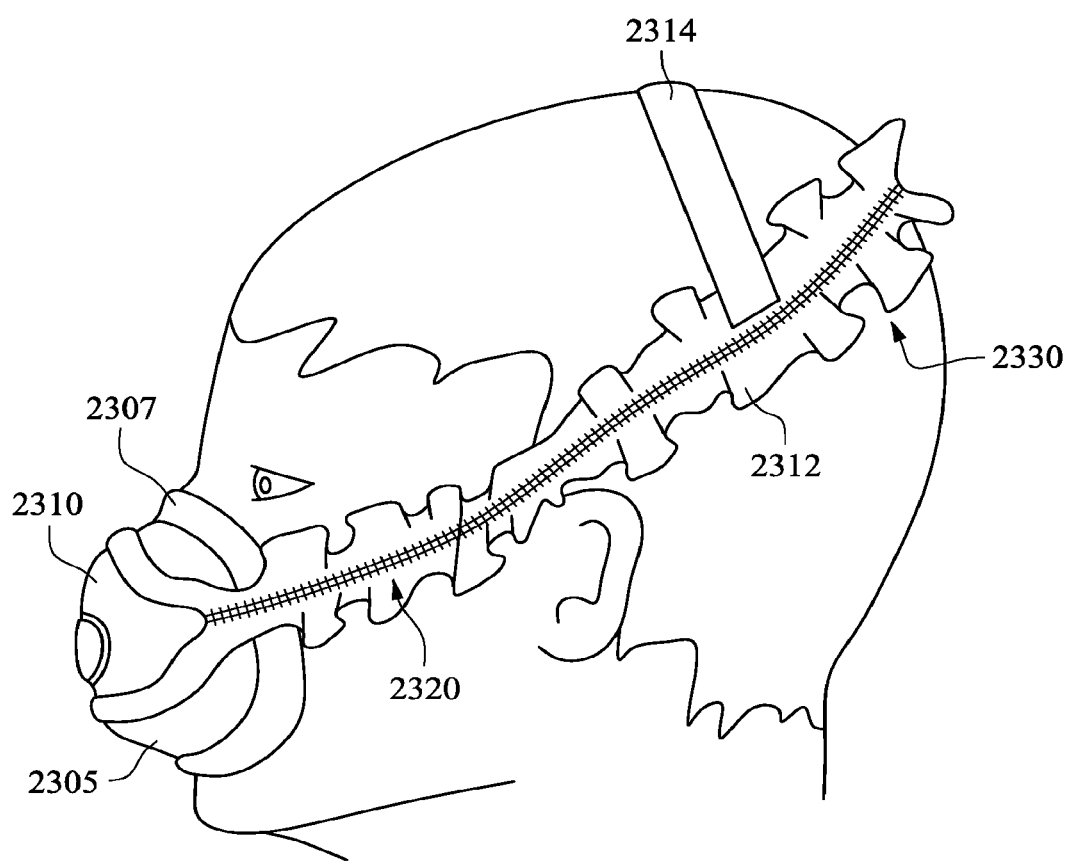
FIG. 24 is a side view of the headgear and mask of FIG. 23.

The number of stitches can be adjusted to enhance comfort, fit and/or performance. For instance, the number of stitches may be varied to create ruffles which may function to reduce facial marking. In the example of FIG. 23, a mask 2305 is supported by headgear 2310. The mask includes a seal portion 2307 which seals against the patient's face. The headgear 2310 includes straps 2312 and may also include an upper strap 2314 to assist in stabilizing the mask. The number of stitches through a middle portion 2320 of the straps 2312 is less than the number of stitches near the outer edge of the straps. The increased number of stitches at the edge portion causes the strap to form ruffles 2330. It will be understood that the number of stitches may be adjusted in any portion of the headgear to achieve a desired fit.

Referring back to FIGS. 13 and 13a, the number of stitches in the rear portion 1310 may be adjusted to cause the rear portion to form a shape configured to conform to a patient's head. The truncated cone shape in FIG. 13 is shown to illustrate an example of adjusting the number of stitches to change the shape. For example, a distal portion 1312 of the rear portion 1310 may have fewer stitches than a proximal portion 1314. In an example, the distal portion may be comprised of 100 stitches and the proximal portion may be comprised of 200 stitches. This arrangement may cause the proximal portion to have an increased diameter thereby flaring outwardly into a truncated cone shape.

2.1.1.4 Variable Thread Count

In another example, the thread count may vary across the fabric to enhance comfort, fit and/or performance. For example, the thread count may be higher in regions requiring greater stiffness (e.g., cheek region, occiput). In regions (e.g., along the straps) where a lower stiffness is desired, however, the thread count may be lower thereby permitting the material to flex more easily.

The thread count, and therefore the stiffness, may be determined by the type of yarn, the type of stitch (e.g., a criss-cross stitch may be stiff), and the distance between stitches.

2.1.1.5 Rigidizer

Figures 1, 25:
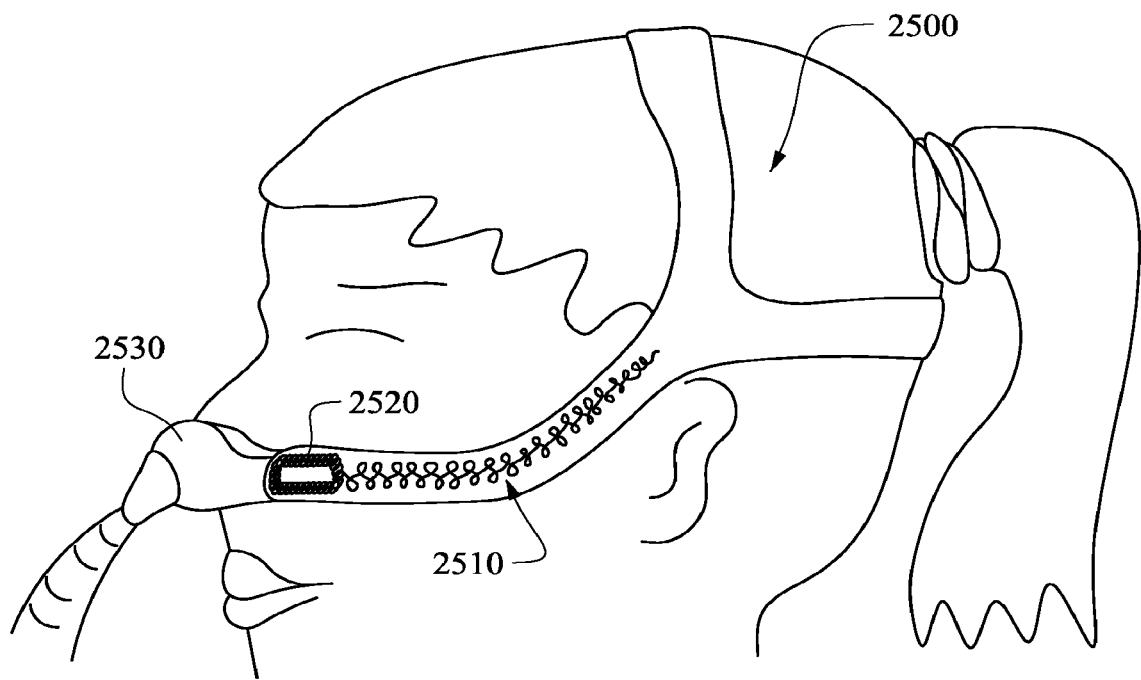
Figures 2, 25:
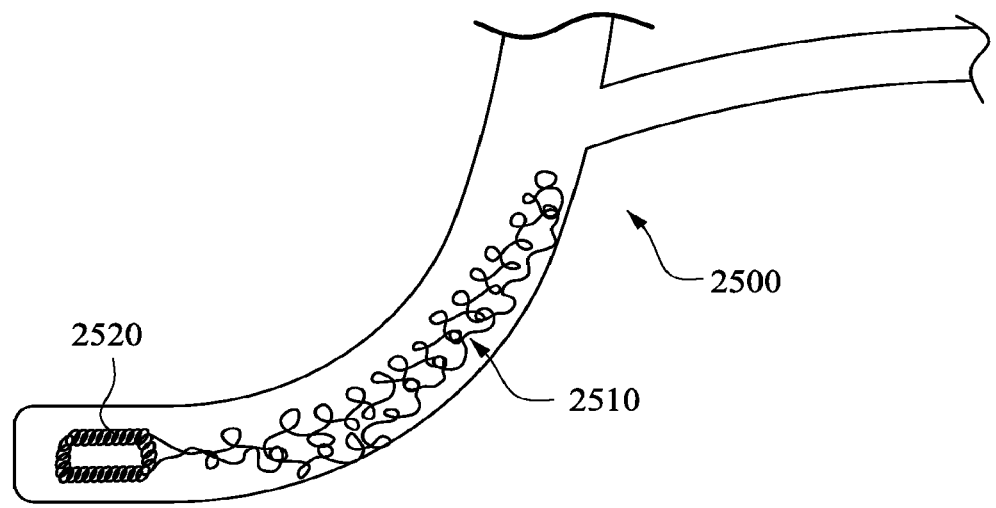

The headgear may include one or more rigidizers that are structured to add rigidity, stiffness and/or stability to the headgear and anchor the headgear in position in use. In an example, a rigidizer is formed integrally with a strap. For instance, in FIGS. 25-1 and 25-2, yarn having a higher stiffness than the surrounding yarn of the headgear 2500 may be knitted in specific regions (e.g., cheek region or crown region) to form a rigidizer 2510. The rigidizer 2510 may stiffen the headgear to provide stability for the mask. In addition, the rigidizer 2510 may be shaped to form a headgear clip 2520 for attachment to a patient interface 2530 (e.g., nasal mask).

Figure 26:
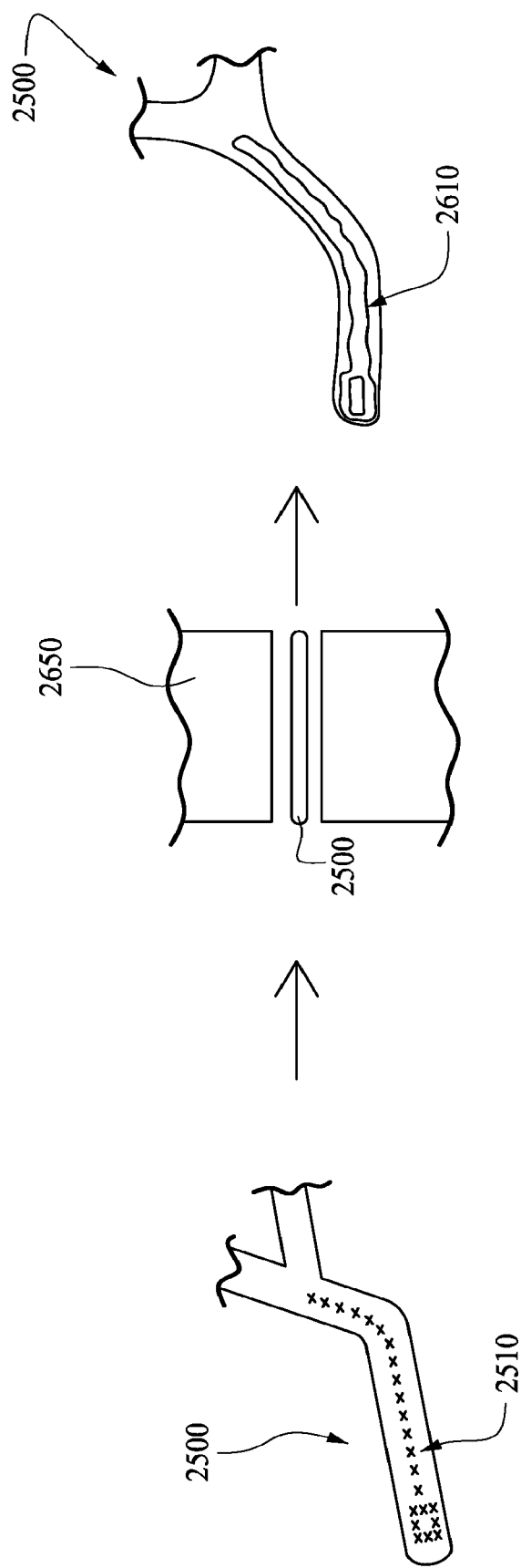
FIG. 26 illustrates a process of forming a rigidizer in headgear according to an example of the disclosed technology.

In another example, the yarn forming the rigidizer 2510 may be melted or fused to further stiffen the yarn into a welded rigidizer 2610, as shown in FIG. 26. Preferably, the rigidizer yarn has a lower melt temperature than the surrounding yarn such that the welded rigidizer 2610 can be formed without deforming the surrounding yarn. In an example, the rigidizer yarn includes polypropylene and the surrounding yarn includes nylon or other non-plastic material such as cotton or wool.

The knitted headgear component may incorporate a thermoplastic yarn that is fused in different regions of the knitted component to impart different properties. By heating the thermoplastic polymer materials, adjacent yarns, filaments, or fibers may fuse to each other in those areas to lock the knit loops together, thereby increasing stiffness or wear-resistance or stability of the mask on the patient's face. As an alternative, the entirety of the knitted headgear component may be formed from yarns that incorporate thermoplastic polymer materials, and only specific portions corresponding with fused areas may be heated to modify the properties.

Figure 27:
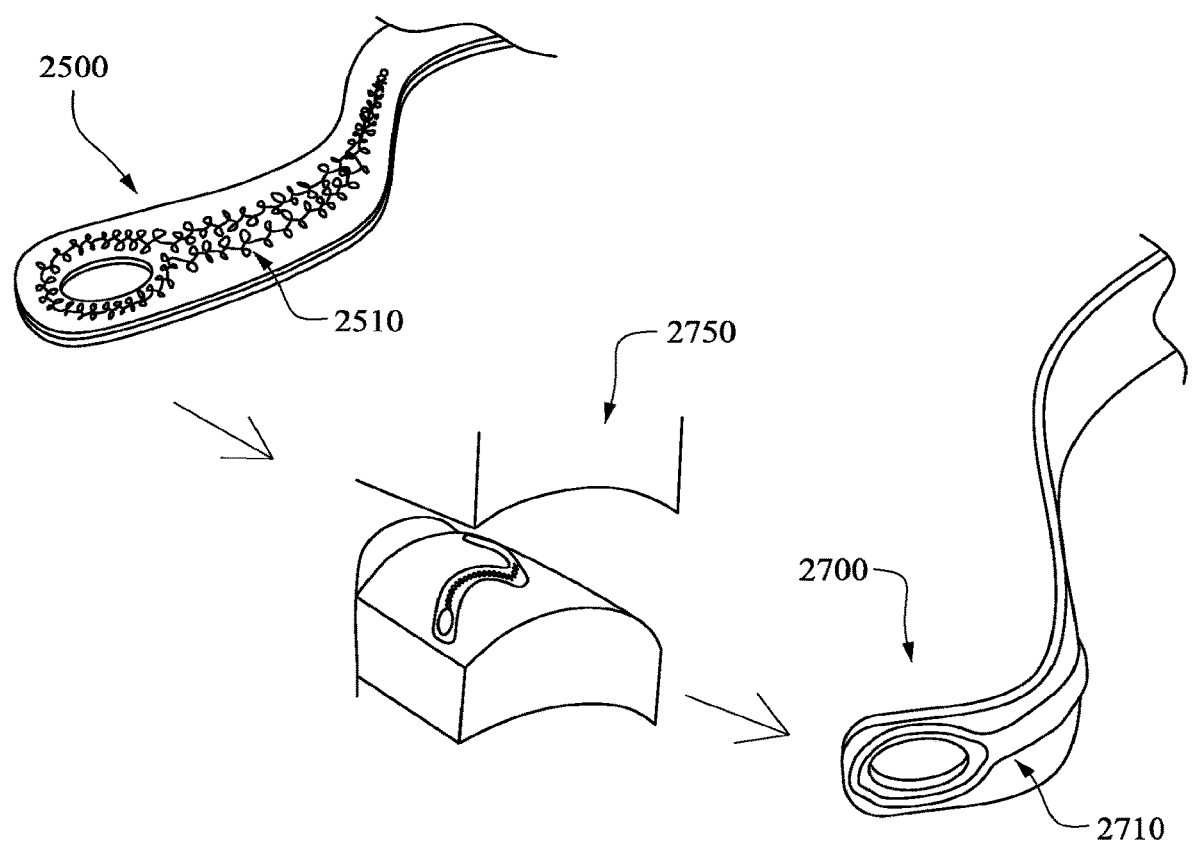
FIG. 27 illustrates a process of forming a curved rigidizer in headgear according to an example of the disclosed technology.

The rigidizer may be formed by a flat tool 2650, as shown in FIG. 26, or a curved tool 2750, as shown in FIG. 27. In FIG. 27, a curved headgear 2700 having a curved rigidizer 2710 is formed.

The inner or outer layer of headgear fabric may be formed to include a slit (or gap). A rigid or semi-rigid element may be inserted through the slit to form a support positioned between the inner layer and the outer layer of the headgear. In an example shown in FIG. 14-5, a similar hollow structure (to FIGS. 14-1 to 14-4) could also be knitted in a flattened-out manner, for instance on a warp knitting machine, by concurrently knitting an outer fabric 461-2, that interfaces with the patient, to a layer of spacer yarns 465-2, which at the same time is knitted to an inner fabric 463-2 that encases the spacer yarns, which is covered in turn by knitting a pocket layer 469-2 that forms a gap 470-2 (or pocket). The pocket layer 469-2 is connected to the outer fabric 461-2, the spacer yarns 465-2 and/or the inner fabric 463-2 only near the selvedge 467-2 of the knitted structure.

Figures 6A, 14:
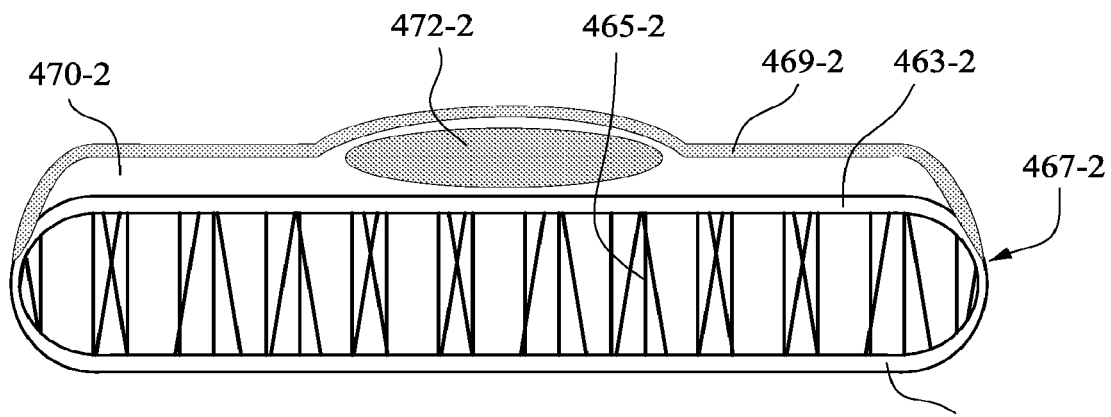

As shown in FIGS. 14-6 and 14-6A, the gap 470-2 could form a hollow pocket in a strap 450-1, for example, which may be filled with a separate rigidizer 472-2, for example, or may be used to locate another related mask component or attachment mechanism. The spacer fabric provides a soft cushioning between a hard part (e.g., the rigidizer 472-2) and the patient's face, and the pocket functions to locate a hard plastic part or cushion attachment into the soft fabric headgear strap encasement, which may be fastened in place by, for example, friction, clips, adhesives, heat laminate or overstitching.

2.1.1.6 Yarn

Yarn may be utilized to create the headgear of the disclosed technology.

The yarn may be synthetic, and may be twisted or textured, and could be made from, but not limited to nylon, polyester, acrylic, rayon, or polypropylene. The yarn could be a conventional staple yarn, a microfiber yarn, or combination of both.

The yarn may incorporate an elastane fiber or filament to provide stretch and recovery properties, such as fibers bearing the LYCRA trademark from the DuPont company.

The yarn may be made of synthetic materials, or natural fibres such as cotton, wool or bamboo, or natural filament such as silk.

The yarns used to construct any component of the headgear may be formed of a monofilament or a plurality of single filaments, that is, a multifilament yarn.

The yarn may include separate filaments that are each formed of different materials. The yarn may also include filaments that are each formed of two or more different materials, such as bicomponent yarn with filaments having a sheath-core configuration or two halves formed of different materials. Different degrees of twist or crimping, as well as different deniers, may affect the properties of the headgear.

The materials utilized to construct the headgear components may be made recyclable or biodegradable, for example, the yarns may include recyclable or biodegradable fibers or filaments.

Areas of the headgear subject to greater wear (for example but not limited to areas or regions coming into contact with a patient's pillow), such as an area of headgear located at the back of the head or nape of the neck, may possibly be more densely fabricated and may thus be a heavier weight and less extensible. Conversely, this area may be subject to the greatest amount of moisture accumulation through sweat, and therefore may need to be made of a thin, yet strong, net-like construction with a custom aperture pattern. In this case, the abrasion-resistance may need to be inherent in the yarn properties only.

2.1.2 3D Printing

Figure 28:
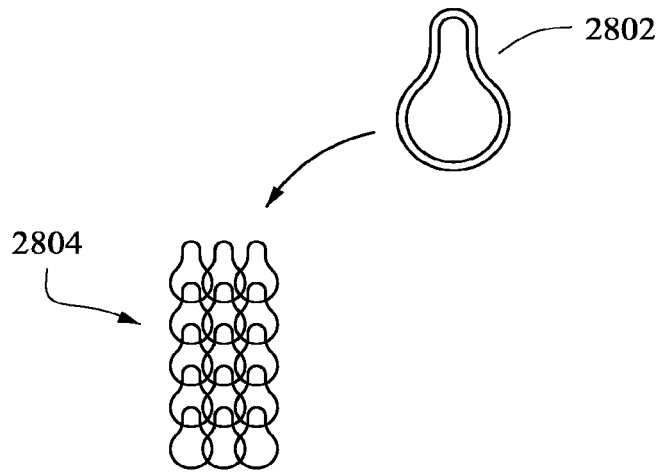
FIG. 28 shows 3D printed links used to form headgear according to an example of the disclosed technology.
Figure 29:
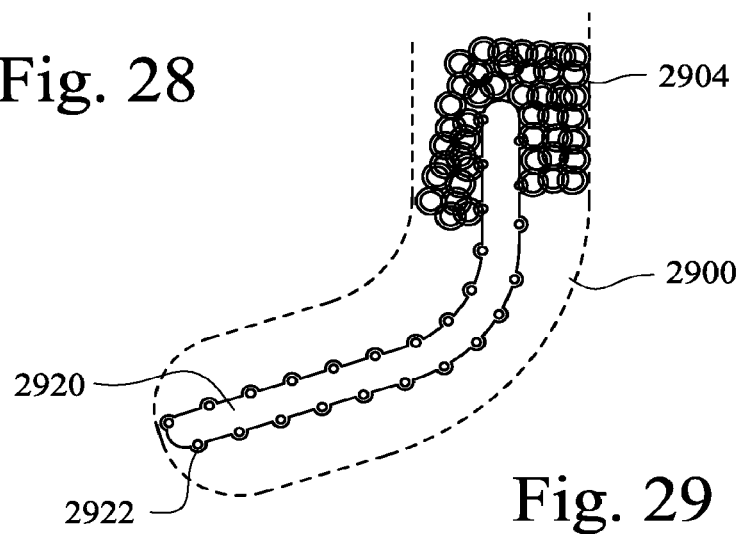
FIG. 29 shows a 3D printed headgear piece including a rigidizer according to an example of the disclosed technology.

In another example, headgear may be manufactured to shape using a 3D printer. As shown in FIG. 28, a 3D printer may be used to print a plurality of connected links 2802 thereby forming a flexible 3D printed textile 2804. Referring to FIG. 29, a headgear piece 2900 may be formed to include a rigidizer 2920. The rigidizer includes holes 2922 through which the links of the textile 2904 may pass as the textile is printed to integrate the textile and the rigidizer. The rigidizer could be made from any suitable material (e.g., a polymer such as Nylon 12 or a sintered solid from a metal powder, or any other material able to used for an additive manufacture process). As the additive manufacture ("3D Printing") process technologies improve, it is envisioned that the material selection will become broader for the purposes of 3D printing textiles, with the optional inclusion of a rigid component. Structure could be inherent in material or by virtue of structure.

Figure 30:
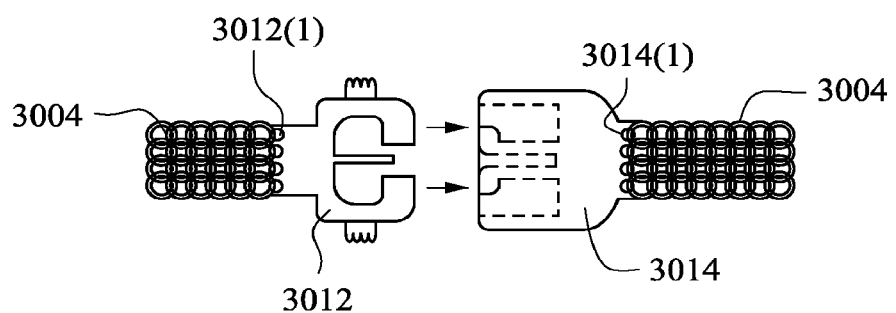
FIG. 30 shows 3D printed headgear straps and clips according to an example of the disclosed technology.

Further, as shown in FIG. 30, a 3D printed strap 3004 may be integrated into holes 3012(1), 3014(1) of male and female clips 3012, 3014.

2.2 Custom Headgear

Custom headgear may be manufactured for an individual patient in accordance with an example of the disclosed technology. Data regarding the shape and size of the patient's head is acquired (e.g., via photo, 3D scan). Measurements that may be used to manufacture a custom headgear may include the circumference of the patient's crown, length from the occiput to the crown, and the position of the patient's ears, eyes and nose. Visual modeling software (e.g., CADCAM) operating on a computer may create a custom headgear model according to the patient's measurements and needs. This model may then be sent to a machine (e.g, a knitting machine or 3D printer) for creation of the headgear.

It is noted that features of the disclosed technology have been particularly described with reference to headgear. However, all of the features described in relation to headgear may also be usable in any mask constructed in accordance with the disclosed technology.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for use in treating a patient for sleep disordered breathing, comprising:
    a mask adapted to seal against the patient's face thereby forming a breathing cavity to deliver pressurized air to the patient's airways; and
    a headgear assembly to support the mask in position on the patient's face for positive pressure treatment of the patient, the headgear assembly including:
        at least one headgear component including spacer fabric having an inner layer, an outer layer and spacer threads joining the inner layer and the outer layer, the inner layer being adapted to interface with the patient and the outer layer forming a non-patient contacting side of the at least one headgear component,
        the inner layer having a first characteristic associated with at least one property and the outer layer having a second characteristic associated with the at least one property, the first characteristic being different from the second characteristic, each spacer thread having a first point along its longitudinal length connected to the inner layer and a second point along its longitudinal length connected to the outer layer, the first point being spaced apart from the second point in a thickness direction of the spacer fabric, wherein lengths of the spacer threads from the respective first points to the respective second points vary along the at least one headgear component to vary a thickness of the spacer fabric so as to form thinner regions and thicker regions of the spacer fabric, and wherein a density of the spacer threads varies along the at least one headgear component to form a first area and a second area, the first area being more dense than the second area, the first area having increased stiffness as compared to the second area and the second area having increased flexibility as compared to the first area.

2. The mask system of claim 1, wherein the at least one property is stretchability, stiffness, flexibility, or hand feel.

3. The mask system of claim 1, wherein the inner layer is configured to be soft and capable of wicking moisture.

4. The mask system of claim 1, wherein the outer layer has a low friction surface to enable movement while sleeping without disrupting the position of the respiratory mask.

5. The mask system of claim 1, wherein the outer layer is elasticated to form a high-tension outer fabric that causes the headgear component to curl upwards and inwards towards the outer layer.

6. The mask system of claim 1, wherein the thickness varies to alter a cushioning effect of the at least one headgear component to correspond to the patient's facial bone/muscle structure and/or to alter breathability.

7. The mask system of claim 1, wherein the at least one headgear component includes at least one thick portion which functions as a rigidizer to provide form to the at least one headgear component.

8. The mask system of claim 1, wherein the spacer fabric has at least one portion that is void of spacer threads, the at least one portion forming a flexible region that is thinner and more flexible than at least one second portion of the spacer fabric.

9. The mask system of claim 8, wherein the flexible region forms a hinge configured to allow the at least one headgear component to bend around a curve of the patient's head in use.

10. The mask system of claim 1, wherein the outer layer includes unbroken loop material.

11. The mask system of claim 1, wherein the spacer threads are shear resistant.

12. The mask system of claim 1, wherein the inner layer is knitted to the outer layer to form a seamless edge.

13. The mask system of claim 1, wherein the inner layer and the outer layer are ultrasonically welded at an edge of the at least one headgear component.

14. The mask system of claim 1, wherein the at least one headgear component comprises a strap.

15. The mask system of claim 1, wherein the at least one headgear component comprises a rear portion adapted to engage the patient's occiput.

16. The mask system of claim 1, wherein the headgear assembly includes at least one crown strap arranged to pass over or around a crown of the patient's head when the mask is worn.

17. The mask system of claim 16, wherein the headgear assembly includes a top strap interconnecting the at least one crown strap and the mask.

18. The mask system of claim 17, wherein the headgear assembly includes a pair of lower headgear straps.

19. The mask system of claim 1, wherein the headgear assembly forms a shape, when the headgear is not being worn, that is configured to conform to the patient's head.

20. The mask system of claim 1, wherein the headgear assembly forms a shape that is configured to conform to the patient's occiput.

* * * * *